US010765390B2

(12) United States Patent
Tajima et al.

(10) Patent No.: US 10,765,390 B2
(45) Date of Patent: Sep. 8, 2020

(54) RADIOGRAPHY SYSTEM, IMAGE PROCESSING APPARATUS, RADIOGRAPHY APPARATUS, IMAGE PROCESSING METHOD, AND IMAGE PROCESSING PROGRAM

(71) Applicant: FUJIFILM CORPORATION, Minato-ku, Tokyo (JP)

(72) Inventors: Takashi Tajima, Kanagawa (JP); Takeshi Kuwabara, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 160 days.

(21) Appl. No.: 16/129,797

(22) Filed: Sep. 13, 2018

(65) Prior Publication Data
US 2019/0008472 A1 Jan. 10, 2019

Related U.S. Application Data

(63) Continuation of application No. PCT/JP2017/006436, filed on Feb. 21, 2017.

(30) Foreign Application Priority Data
Mar. 28, 2016 (JP) .................................. 2016-063952

(51) Int. Cl.
*A61B 6/00* (2006.01)
(52) U.S. Cl.
CPC ............ *A61B 6/505* (2013.01); *A61B 6/4266* (2013.01); *A61B 6/482* (2013.01); *A61B 6/5235* (2013.01); *A61B 6/5258* (2013.01)

(58) Field of Classification Search
CPC ....... A61B 6/4266; A61B 6/482; A61B 6/505; A61B 6/5235; A61B 6/5258
See application file for complete search history.

(56) References Cited

U.S. PATENT DOCUMENTS

| 5,910,972 A | 6/1999 | Ohkubo et al. |
| 7,330,531 B1 * | 2/2008 | Karellas ............... A61B 6/4241 |
| | | 250/370.09 |

(Continued)

FOREIGN PATENT DOCUMENTS

| JP | H06-189951 A | 7/1994 |
| JP | H10-155115 A | 6/1998 |

(Continued)

OTHER PUBLICATIONS

International Search Report issued in International Application No. PCT/JP2017/006436 dated May 23, 2017.

(Continued)

*Primary Examiner* — Chih-Cheng Kao
(74) *Attorney, Agent, or Firm* — SOLARIS Intellectual Property Group, PLLC

(57) ABSTRACT

A control unit of a console performs a first correction process for generating a diagnosis image for a second radiographic image captured by a second radiation detector and generates the diagnosis image, using the second radiographic image subjected to the first correction process and a first radiographic image captured by a first radiation detector. The control unit performs a second correction process for deriving a quantitative value for the second radiographic image captured by the second radiation detector and derives bone density, using the second radiographic image subjected to the second correction process and the first radiographic image captured by the first radiation detector.

11 Claims, 10 Drawing Sheets

(56) References Cited

U.S. PATENT DOCUMENTS

| | | |
|---|---|---|
| 2015/0131777 A1 | 5/2015 | Makifuchi et al. |
| 2018/0028139 A1* | 2/2018 | Kuwabara ............ A61B 6/4266 |
| 2018/0031715 A1* | 2/2018 | Kuwabara ................. G01T 7/00 |
| 2019/0011576 A1* | 1/2019 | Kuwabara ............... G01T 1/208 |

FOREIGN PATENT DOCUMENTS

| | | |
|---|---|---|
| JP | 2011-056257 A | 3/2011 |
| WO | 2013/187150 A1 | 12/2013 |

OTHER PUBLICATIONS

Written Opinion of the ISA issued in International Application No. PCT/JP2017/006436 dated May 23, 2017.

\* cited by examiner

PLAN VIEW ILLUSTRATING EACH RADIATION DETECTOR
AS VIEWED FROM EMISSION SIDE OF RADIATION R

RADIOGRAPHY SYSTEM, IMAGE PROCESSING APPARATUS, RADIOGRAPHY APPARATUS, IMAGE PROCESSING METHOD, AND IMAGE PROCESSING PROGRAM

CROSS-REFERENCE TO RELATED APPLICATION

This application is a continuation application of International Application No. PCT/JP2017/006436, filed Feb. 21, 2017, the disclosure of which is incorporated herein by reference in its entirety. Further, this application claims priority from Japanese Patent Application No. 2016-063952 filed Mar. 28, 2016, the disclosure of which is incorporated herein by reference in their entirety.

BACKGROUND OF THE INVENTION

1. Field of the Invention

The present disclosure relates to a radiography system, an image processing apparatus, a radiography apparatus, an image processing method, and an image processing program.

2. Description of the Related Art

In the related art, a radiography apparatus has been known which includes a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation. In addition, a technique has been known which derives the bone density of a subject using the detection results of each radiation detector in this type of radiography apparatus (see JP2011-056257A).

SUMMARY OF THE INVENTION

However, in a case in which the two radiation detectors are used to capture radiographic images, radiation which has been transmitted through the radiation detector provided on the incident side of radiation reaches the radiation detector provided on the emission side of radiation. Therefore, the amount of radiation that reaches the radiation detector provided on the emission side of radiation is less than the amount of radiation that reaches the radiation detector provided on the incident side and the amount of radiation used to generate a radiographic image is reduced.

Therefore, the influence of noise on the radiographic image captured by the radiation detector provided on the emission side of radiation is more than the influence of noise on the radiographic image captured by the radiation detector provided on the incident side of radiation.

The present disclosure provides a radiography system, an image processing apparatus, a radiography apparatus, an image processing method, and an image processing program that can obtain a high-quality diagnosis image and at least one of a high-accuracy bone mineral content value or bone density.

According to a first aspect of the invention, there is provided a radiography system comprising: a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation; a generation unit that performs a first correction process for generating a diagnosis image for a second radiographic image captured by the second radiation detector and generates the diagnosis image, using the second radiographic image subjected to the first correction process and a first radiographic image captured by the first radiation detector; and a derivation unit that performs a second correction process for deriving a quantitative value for the second radiographic image captured by the second radiation detector and derives at least one of bone mineral content or bone density, using the second radiographic image subjected to the second correction process and the first radiographic image captured by the first radiation detector.

According to a second aspect of the invention, there is provided a radiography system comprising: a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation; a control unit that performs first control including control for reading charge from a plurality of pixels of the first radiation detector and control for reading charge from a plurality of pixels of the second radiation detector and performing a first correction process for generating a diagnosis image for image data obtained by the read charge in a case in which the diagnosis image is generated and performs second control including control for reading charge from the plurality of pixels of the first radiation detector and control for reading charge from the plurality of pixels of the second radiation detector and performing a second correction process for deriving a quantitative value for image data obtained by the read charge in a case in which the quantitative value is derived; a generation unit that generates the diagnosis image, using a first radiographic image and a second radiographic image obtained by the first control; and a derivation unit that derives at least one of bone mineral content or bone density, using a first radiographic image and a second radiographic image obtained by the second control.

According to a third aspect of the invention, in the radiography system according to the first or second aspect, the second correction process may be at least one of a correction process in which the amount of noise removed is more than the amount of noise removed in the first correction process or a correction process in which the amount of noise allowed in a processing result is less than the amount of noise allowed in a processing result of the first correction process.

According to a fourth aspect of the invention, in the radiography system according to any one of the first to third aspects, the first correction process may be a correction process that removes a visible artifact in the diagnosis image.

According to a fifth aspect of the invention, in the radiography system according to any one of the first to fourth aspects, the second correction process may be a correction process that prevents a variation in an average value of pixel values in each of a soft tissue region and a bone tissue region of the corrected second radiographic image in each imaging operation.

According to a sixth aspect of the invention, the radiography system according to any one of the first to fifth aspects may further comprise a radiation limitation member that limits the transmission of the radiation between the first radiation detector and the second radiation detector.

According to a seventh aspect of the invention, in the radiography system according to any one of the first to sixth aspects, each of the first radiation detector and the second radiation detector may comprise a light emitting layer that is irradiated with the radiation and emits light. The plurality of pixels of each of the first radiation detector and the second radiation detector may receive the light, generate the charge, and accumulate the charge. The light emitting layer of the first radiation detector and the light emitting layer of the second radiation detector may have different compositions.

According to an eighth aspect of the invention, in the radiography system according to any one of the first to sixth aspects, each of the first radiation detector and the second radiation detector may comprise a light emitting layer that is irradiated with the radiation and emits light and a substrate provided with the plurality of pixels which receive the light, generate the charge, and accumulate the charge. The substrate may be stacked on a side of the light emitting layer on which the radiation is incident.

According to a ninth aspect of the invention, in the radiography system according to any one of the first to eighth aspects, the light emitting layer of the first radiation detector may include CsI and the light emitting layer of the second radiation detector may include GOS.

According to a tenth aspect of the invention, there is provided an image processing apparatus comprising: an acquisition unit that acquires a first radiographic image and a second radiographic image from a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation; a generation unit that performs a first correction process for generating a diagnosis image for the second radiographic image captured by the second radiation detector and generates the diagnosis image, using the second radiographic image subjected to the first correction process and the first radiographic image captured by the first radiation detector; and a derivation unit that performs a second correction process for deriving a quantitative value for the second radiographic image captured by the second radiation detector and derives at least one of bone mineral content or bone density, using the second radiographic image subjected to the second correction process and the first radiographic image captured by the first radiation detector.

According to an eleventh aspect of the invention, there is provided a radiography apparatus comprising: a first radiation detector that includes a plurality of pixels accumulating charge corresponding to emitted radiation; a second radiation detector that is provided so as to be stacked on a side of the first radiation detector from which the radiation is transmitted and emitted and includes a plurality of pixels accumulating charge corresponding to the emitted radiation; and a control unit that performs first control including control for reading charge from a plurality of pixels of the first radiation detector and control for reading charge from a plurality of pixels of the second radiation detector and performing a first correction process for generating a diagnosis image for image data obtained by the read charge in a case in which the diagnosis image is generated and performs second control including control for reading charge from the plurality of pixels of the first radiation detector and control for reading charge from the plurality of pixels of the second radiation detector and performing a second correction process for deriving a quantitative value for image data obtained by the read charge in a case in which the quantitative value is derived.

According to a twelfth aspect of the invention, there is provided an image processing method comprising: allowing an acquisition unit to acquire a first radiographic image and a second radiographic image from a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation; allowing a generation unit to perform a first correction process for generating a diagnosis image for the second radiographic image captured by the second radiation detector and to generate the diagnosis image, using the second radiographic image subjected to the first correction process and the first radiographic image captured by the first radiation detector; and allowing a derivation unit to perform a second correction process for deriving a quantitative value for the second radiographic image captured by the second radiation detector and to derive at least one of bone mineral content or bone density, using the second radiographic image subjected to the second correction process and the first radiographic image captured by the first radiation detector.

According to a thirteenth aspect of the invention, there is provided an image processing program that causes a computer to perform a process comprising: acquiring a first radiographic image and a second radiographic image from a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation; performing a first correction process for generating a diagnosis image for the second radiographic image captured by the second radiation detector and generating the diagnosis image, using the second radiographic image subjected to the first correction process and the first radiographic image captured by the first radiation detector; and performing a second correction process for deriving a quantitative value for the second radiographic image captured by the second radiation detector and deriving at least one of bone mineral content or bone density, using the second radiographic image subjected to the second correction process and the first radiographic image captured by the first radiation detector.

According to an embodiment of the invention, it is possible to provide a radiography system, an image processing apparatus, a radiography apparatus, an image processing method, and an image processing program that can obtain a high-quality diagnosis image and at least one of a high-accuracy bone mineral content value or bone density.

DESCRIPTION OF THE PREFERRED EMBODIMENTS

Hereinafter, embodiments of the present disclosure will be described in detail with reference to the drawings.

First Embodiment

Figure 1:
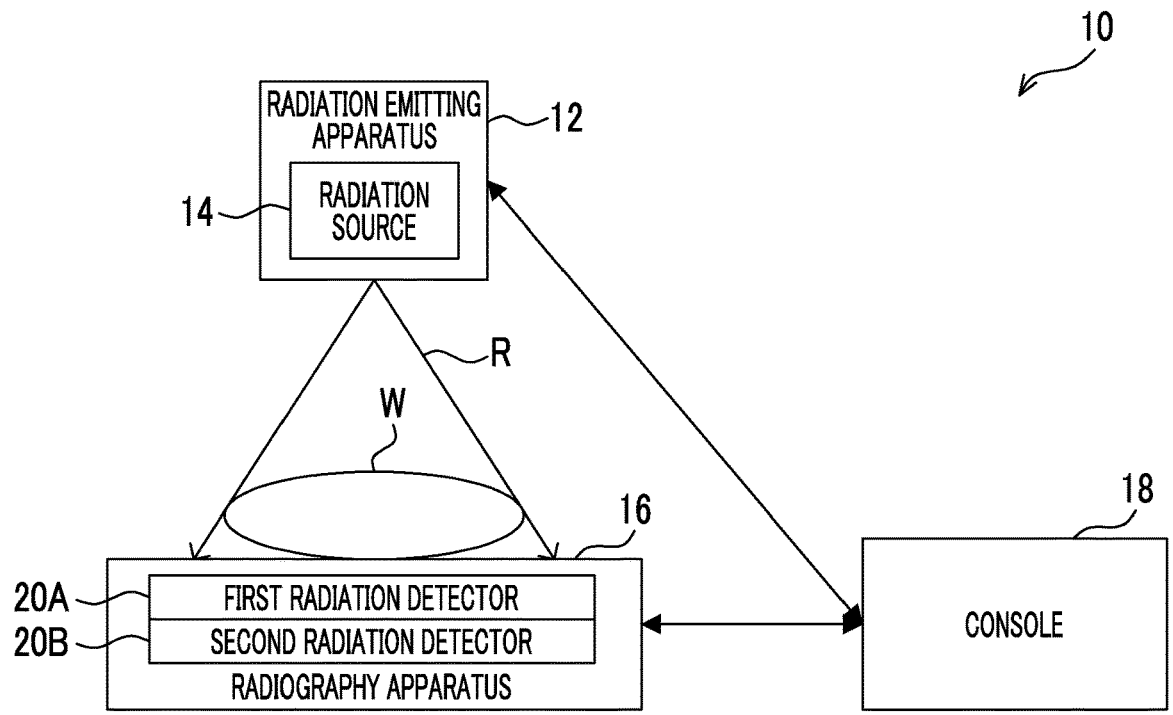
FIG. 1 is a block diagram illustrating an example of the configuration of a radiography system according to a first embodiment.

First, the configuration of a radiography system 10 according to this embodiment will be described with reference to FIG. 1. As illustrated in FIG. 1, the radiography system 10 includes a radiation emitting apparatus 12, a radiography apparatus 16, and a console 18. The console 18 according to this embodiment is an example of an image processing apparatus according to the present disclosure.

The radiation emitting apparatus 12 according to this embodiment includes a radiation source 14 that irradiates a subject W, which is an example of an imaging target, with radiation R such as X-rays. An example of the radiation emitting apparatus 12 is a treatment cart. A method for commanding the radiation emitting apparatus 12 to emit the radiation R is not particularly limited. For example, in a case in which the radiation emitting apparatus 12 includes an irradiation button, a user, such as a doctor or a radiology technician, may press the irradiation button to command the emission of the radiation R such that the radiation R is emitted from the radiation emitting apparatus 12. In addition, for example, the user may operate the console 18 to command the emission of the radiation R such that the radiation R is emitted from the radiation emitting apparatus 12.

In a case in which the command to emit the radiation R is received, the radiation emitting apparatus 12 emits the radiation R from the radiation source 14 according to set emission conditions, such as a tube voltage, a tube current, and an irradiation period.

The radiography apparatus 16 according to this embodiment includes a first radiation detector 20A and a second radiation detector 20B that detect the radiation R which has been emitted from the radiation emitting apparatus 12 and then transmitted through the subject W. The radiography apparatus 16 captures radiographic images of the subject W using the first radiation detector 20A and the second radiation detector 20B. Hereinafter, in a case in which the first radiation detector 20A and the second radiation detector 20B do not need to be distinguished from each other, they are generically referred to as "radiation detectors 20".

Figure 2:
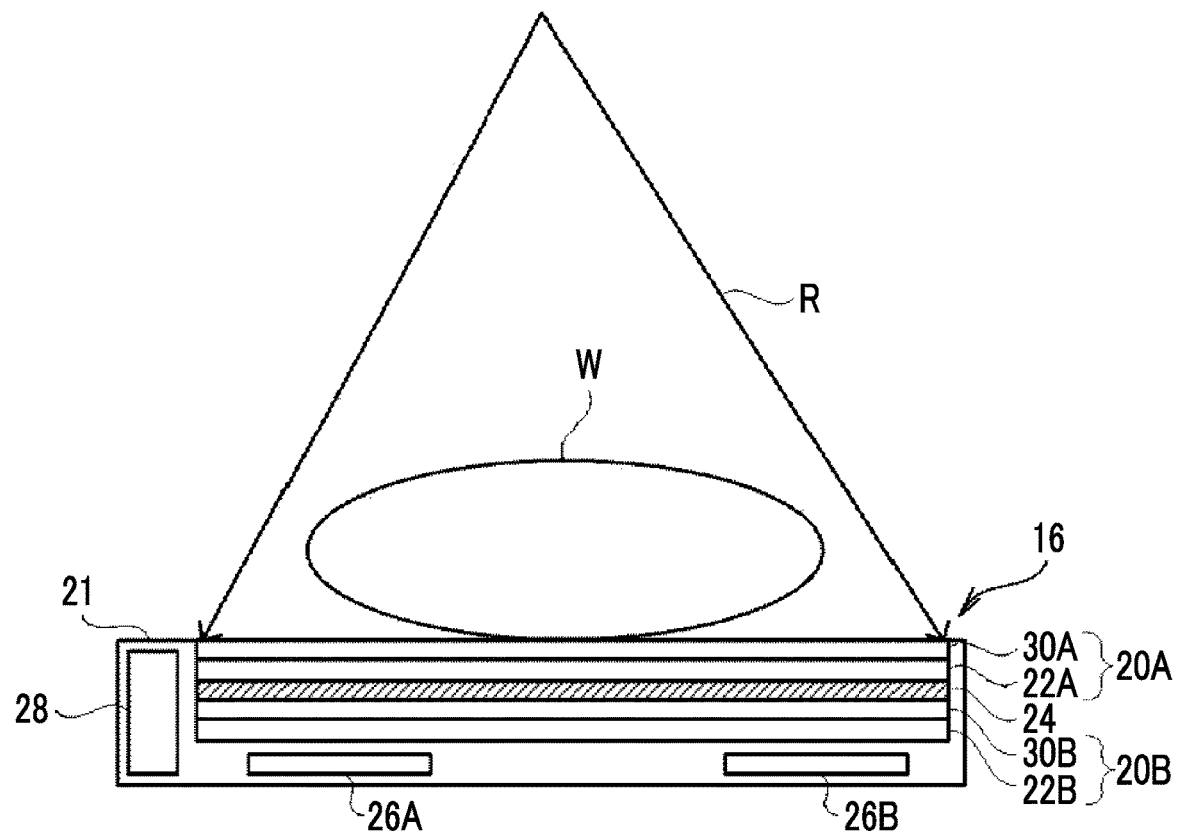
FIG. 2 is a cross-sectional view illustrating an example of the configuration of a radiography apparatus according to the first embodiment.

Next, the configuration of the radiography apparatus 16 according to this embodiment will be described with reference to FIG. 2. As illustrated in FIG. 2, the radiography apparatus 16 includes a plate-shaped housing 21 that transmits the radiation R and has a waterproof, antibacterial, and airtight structure. The housing 21 includes the first radiation detector 20A, the second radiation detector 20B, a radiation limitation member 24, a control substrate 26A, a control substrate 26B, and a case 28.

The first radiation detector 20A is provided on the incident side of the radiation R in the radiography apparatus 16 and the second radiation detector 20B is provided so as to be stacked on the side of the first radiation detector 20A from which the radiation R is transmitted and emitted. The first radiation detector 20A includes a thin film transistor (TFT) substrate 30A and a scintillator 22A which is an example of a light emitting layer that is irradiated with the radiation R and emits light corresponding to the amount of emitted radiation R. The TFT substrate 30A and the scintillator 22A are stacked in the order of the TFT substrate 30A and the scintillator 22A from the incident side of the radiation R.

The second radiation detector 20B includes a TFT substrate 30B and a scintillator 22B which is an example of the light emitting layer. The TFT substrate 30B and the scintillator 22B are stacked in the order of the TFT substrate 30B and the scintillator 22B from the incident side of the radiation R.

That is, the first radiation detector 20A and the second radiation detector 20B are so-called irradiation side sampling (ISS) radiation detectors that are irradiated with the radiation R from the TFT substrates 30A and 30B.

In the radiography apparatus 16 according to this embodiment, the scintillator 22A of the first radiation detector 20A and the scintillator 22B of the second radiation detector 20B have different compositions. Specifically, for example, the composition of the scintillator 22A includes CsI (Tl) (cesium iodide having thallium added thereto) as a main component and the composition of the scintillator 22B includes gadolinium oxysulfide (GOS) as a main component. GOS is more sensitive to the high-energy radiation R than CsI. In addition, a combination of the composition of the scintillator 22A and the composition of the scintillator 22B is not limited to the above-mentioned example and may be a combination of other compositions or a combination of the same compositions.

The radiation limitation member 24 that limits the transmission of the radiation R is provided between the first radiation detector 20A and the second radiation detector 20B. An example of the radiation limitation member 24 is a plate-shaped member made of, for example, copper or tin. It is preferable that a variation in the thickness of the radiation limitation member 24 in the incident direction of the radiation R is equal to or less than 1% in order to uniformize in the limitation (transmittance) of radiation.

The control substrate 26A is provided so as to correspond to the first radiation detector 20A and electronic circuits, such as an image memory 56A and a control unit 58A which will be described below, are formed on the control substrate 26A. The control substrate 26B is provided so as to correspond to the second radiation detector 20B and electronic circuits, such as an image memory 56B and a control unit 58B which will be described below, are formed on the control substrate 26B. The control substrate 26A and the control substrate 26B are provided on the side of the second radiation detector 20B which is opposite to the incident side of the radiation R.

As illustrated in FIG. 2, the case 28 is provided at a position (that is, outside the range of an imaging region) that does not overlap the radiation detector 20 at one end of the housing 21. For example, a power supply unit 70 which will be described below is accommodated in the case 28. The installation position of the case 28 is not particularly limited. For example, the case 28 may be provided at a position that overlaps the radiation detector 20 on the side of the second radiation detector 20B which is opposite to the incident side of the radiation.

Next, the configuration of a main portion of an electric system of the radiography apparatus 16 according to this embodiment will be described with reference to FIG. 3.

Figure 3:
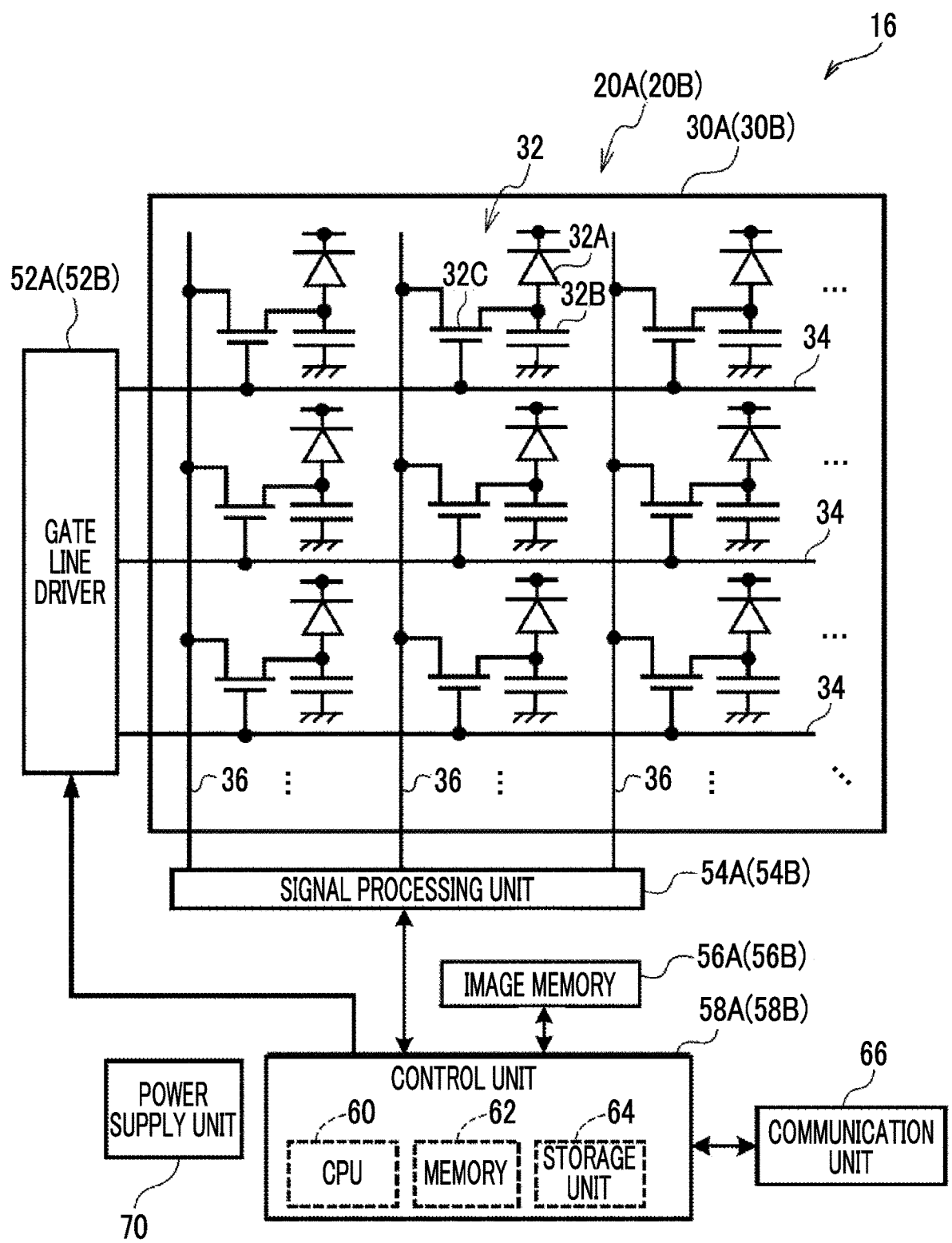
FIG. 3 is a block diagram illustrating an example of the configuration of a main portion of an electric system of the radiography apparatus according to the first embodiment.

As illustrated in FIG. 3, a plurality of pixels 32 are two-dimensionally provided in one direction (a row direction in FIG. 3) and a cross direction (a column direction in FIG. 3) that crosses the one direction on the TFT substrate 30A. The pixel 32 includes a sensor unit 32A, a capacitor 32B, and a field effect thin film transistor (TFT; hereinafter, simply referred to as a "thin film transistor") 32C.

The sensor unit 32A includes, for example, an upper electrode, a lower electrode, and a photoelectric conversion film which are not illustrated, absorbs the light emitted from the scintillator 22A, and generates charge. The capacitor 32B accumulates the charge generated by the sensor unit 32A. The thin film transistor 32C reads the charge accumulated in the capacitor 32B in response to a control signal and outputs the charge.

A plurality of gate lines 34 which extend in the one direction and are used to turn each thin film transistor 32C on and off are provided on the TFT substrate 30A. In addition, a plurality of data lines 36 which extend in the cross direction and through which the charge read by the thin film transistors 32C in an on state are output are provided on the TFT substrate 30A.

Each gate line 34 of the TFT substrate 30A is connected to a gate line driver 52A and each data line 36 of the TFT substrate 30A is connected to a signal processing unit 54A.

The thin film transistors 32C connected to each gate line 34 (in this embodiment, each row in FIG. 3) in the TFT substrate 30A are sequentially turned on by the control signals which are supplied from the gate line driver 52A through the gate lines 34. Then, the charge which has been read by the thin film transistor 32C in an on state is transmitted as an electric signal through the data line 36 and is input to the signal processing unit 54A. In this way, charge is sequentially read from each gate line 34 (in this embodiment, each row illustrated in FIG. 3) and image data indicating a two-dimensional radiographic image is acquired.

The signal processing unit 54A includes amplifying circuits (not illustrated) for amplifying an input electric signal and sample-and-hold circuits (not illustrated) which are provided for each data line 36. The electric signal transmitted through each data line 36 is amplified by the amplifying circuit and is then held by the sample-and-hold circuit. A multiplexer (not illustrated) and an analog/digital (A/D) converter (not illustrated) are connected to the output side of the sample-and-hold circuit in this order. The electric signals held by each sample-and-hold circuit are sequentially (serially) input to the multiplexer and are sequentially selected by the multiplexer. Then, the selected electric signal is converted into digital image data by the A/D converter.

An image memory 56A is connected to the signal processing unit 54A. The image data output from the A/D converter of the signal processing unit 54A is sequentially output to the control unit 58A. The image memory 56A is connected to the control unit 58A. The image data sequentially output from the signal processing unit 54A is sequentially stored in the image memory 56A under the control of the control unit 58A. The image memory 56A has memory capacity that can store a predetermined amount of image data. Whenever a radiographic image is captured, captured image data is sequentially stored in the image memory 56A. In addition, the image memory 56A is also connected to the control unit 58A.

The control unit 58A includes a central processing unit (CPU) 60, a memory 62 including, for example, a read only memory (ROM) and a random access memory (RAM), and a non-volatile storage unit 64 such as a flash memory. An example of the control unit 58A is a microcomputer.

A communication unit 66 is connected to the control unit 58A and transmits and receives various kinds of information to and from external apparatuses, such as the radiation emitting apparatus 12 and the console 18, using at least one of wireless communication or wired communication. The power supply unit 70 supplies power to each of the above-mentioned various circuits or elements (for example, the gate line driver 52A, the signal processing unit 54A, the image memory 56A, the control unit 58A, and the communication unit 66). In FIG. 3, lines for connecting the power supply unit 70 to various circuits or elements are not illustrated in order to avoid complication.

Components of the TFT substrate 30B, the gate line driver 52B, the signal processing unit 54B, the image memory 56B, and the control unit 58B of the second radiation detector 20B have the same configurations as the corresponding components of the first radiation detector 20A, and thus the description thereof will not be repeated here. In addition, the control unit 58A and the control unit 58B are connected such that they can communicate with each other.

With the above-mentioned configuration, the radiography apparatus 16 according to this embodiment captures radiographic images using the first radiation detector 20A and the second radiation detector 20B.

Figure 4:
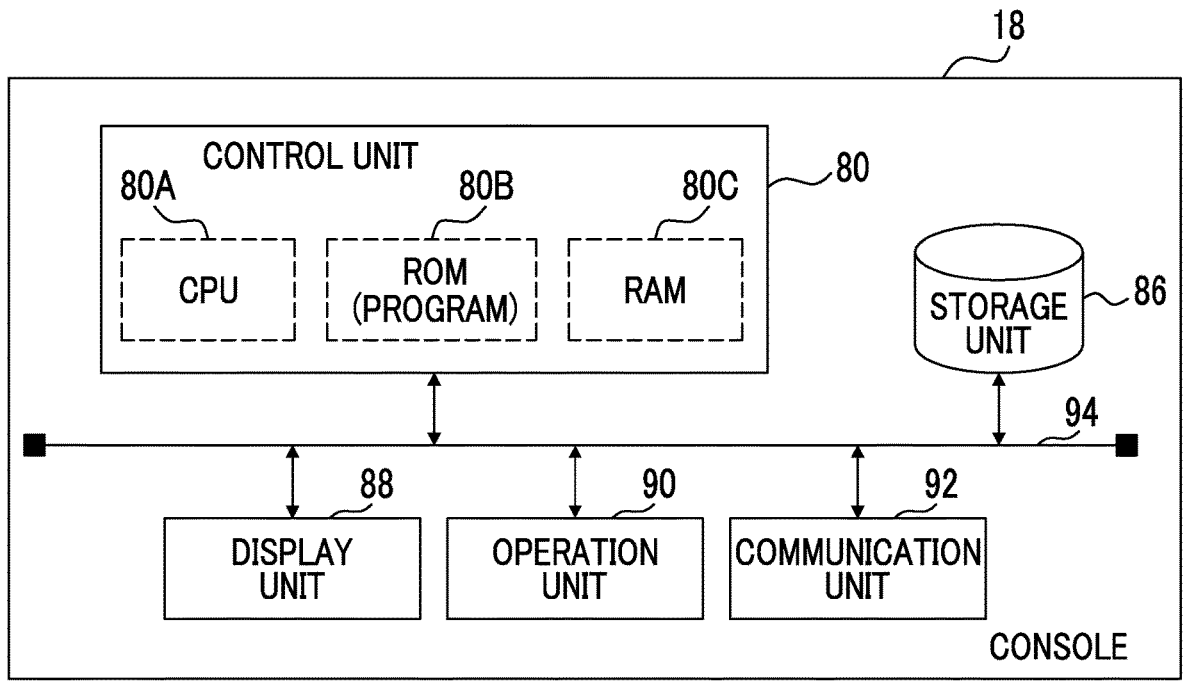
FIG. 4 is a block diagram illustrating an example of the configuration of a main portion of an electric system of a console according to the first embodiment.

Next, the configuration of the console 18 according to this embodiment will be described with reference to FIG. 4. As illustrated in FIG. 4, the console 18 includes a control unit 80. The control unit 80 includes a CPU 80A that controls the overall operation of the console 18, a ROM 80B in which, for example, various programs or various parameters are stored in advance, and a RAM 80C that is used as, for example, a work area when the CPU 80A executes various programs.

The console 18 further includes a non-volatile storage unit 86 such as a hard disk drive (HDD). The storage unit 86 stores and holds image data indicating the radiographic image captured by the first radiation detector 20A, image data indicating the radiographic image captured by the second radiation detector 20B, and various other types of data. Hereinafter, the radiographic image captured by the first radiation detector 20A is referred to as a "first radiographic image" and image data indicating the first radiographic image is referred to as "first radiographic image data". In addition, hereinafter, the radiographic image captured by the second radiation detector 20B is referred to as a "second radiographic image" and image data indicating the second radiographic image is referred to as "second radiographic image data". Furthermore, in a case in which the "first radiographic image" and the "second radiographic image" are generically referred to, they are simply referred to as "radiographic images".

The console 18 includes a display unit 88, an operation unit 90, and a communication unit 92. The display unit 88 displays, for example, information related to imaging or the radiographic image obtained by imaging. The operation unit 90 is used by the user to input, for example, a command to capture a radiographic image and a command related to image processing for the captured radiographic image. For example, the operation unit 90 may have the form of a keyboard or may have the form of a touch panel that is integrated with the display unit 88. The communication unit 92 transmits and receives various kinds of information to and from external systems, such as a picture archiving and communication system (PACS) and a radiology information system (RIS), using at least one of wireless communication or wired communication. In addition, the communication unit 92 transmits and receives various kinds of information to and from the radiography apparatus 16 and the radiation emitting apparatus 12, using at least one of wireless communication or wired communication.

The control unit 80, the storage unit 86, the display unit 88, the operation unit 90, and the communication unit 92 are connected to each other through a bus 94.

In the radiography apparatus 16 according to this embodiment, since the first radiation detector 20A and the radiation limitation member 24 absorb the radiation R, the amount of radiation that reaches the second radiation detector 20B is less than the amount of radiation that reaches the first radiation detector 20A.

In this embodiment, for example, about 50% of the radiation R that has reached the first radiation detector 20A is absorbed by the first radiation detector 20A and is used to capture a radiographic image. In addition, about 60% of the radiation R that has been transmitted through the first radiation detector 20A and reached the radiation limitation member 24 is absorbed by the radiation limitation member 24. About 50% of the radiation R that has been transmitted through the first radiation detector 20A and the radiation limitation member 24 and reached the second radiation detector 20B is absorbed by the second radiation detector 20B and is used to capture a radiographic image.

That is, the amount of radiation (the amount of charge generated by the second radiation detector 20B) used by the second radiation detector 20B to capture a radiographic image is about 20% of the amount of radiation used by the first radiation detector 20A to capture a radiographic image. In addition, the ratio of the amount of radiation used by the second radiation detector 20B to capture a radiographic image to the amount of radiation used by the first radiation detector 20A to capture a radiographic image is not limited to the above-mentioned ratio. However, it is preferable that the amount of radiation used by the second radiation detector 20B to capture a radiographic image is equal to or greater than 10% of the amount of radiation used by the first radiation detector 20A to capture a radiographic image in terms of diagnosis.

Figure 5:
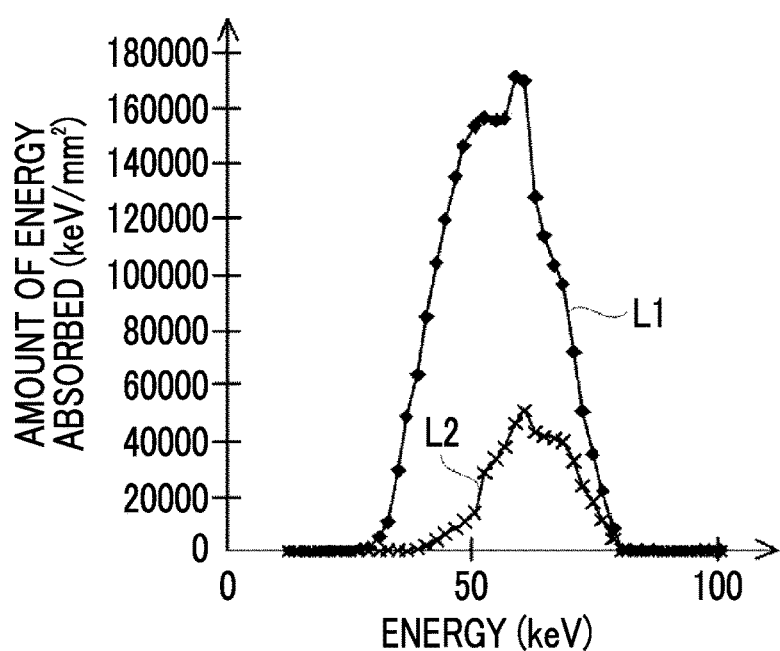
FIG. 5 is a graph illustrating the amount of radiation that reaches each of a first radiation detector and a second radiation detector according to the first embodiment.

Low-energy components of the radiation R are absorbed first. Therefore, for example, as illustrated in FIG. 5, the energy components of the radiation R that reaches the second radiation detector 20B do not include the low-energy components of the energy components of the radiation R that reaches the first radiation detector 20A. In FIG. 5, the vertical axis indicates the amount of radiation R absorbed per unit area and the horizontal axis indicates the energy of the radiation R in a case in which the tube voltage of the radiation source 14 is 80 kV. In addition, in FIG. 5, a solid line L1 indicates the relationship between the energy of the radiation R absorbed by the first radiation detector 20A and the amount of radiation R absorbed per unit area. In FIG. 5, a solid line L2 indicates the relationship between the energy of the radiation R absorbed by the second radiation detector 20B and the amount of radiation R absorbed per unit area.

As such, the amounts of radiation used for imaging are different in the first radiation detector 20A and the second radiation detector 20B. In addition, the energy components of the radiation R that reach the first radiation detector 20A and the second radiation detector 20B are different from each other.

There is a difference between the amount of radiation R absorbed by a bone tissue and the amount of radiation R absorbed by a soft tissue. As the level of the energy of the radiation R used for imaging becomes lower, the ratio of the pixel value of the bone tissue to the pixel value of the soft tissue in the radiographic image becomes higher. In addition, the absorptivity of a low-energy component in the soft tissue is higher than that in the bone tissue.

In contrast, as illustrated in FIG. 5, since the radiation R that reaches the first radiation detector 20A includes a high-energy component and a low-energy component, the first radiographic image captured by the first radiation detector 20A is a radiographic image in which soft tissues and bone tissues can be easily seen as in normal imaging. On the other hand, as illustrated in FIG. 5, since low-energy components are reduced in the radiation R that reaches the second radiation detector 20B, the second radiographic image captured by the second radiation detector 20B is a radiographic image in which are bone tissues are highlighted.

Therefore, the first radiographic image captured by the first radiation detector 20A and the second radiographic image captured by the second radiation detector 20B are visually different even though they are images of the same subject W.

The control unit 80 of the console 18 according to this embodiment generates image data indicating an energy subtraction image, using the first radiographic image captured by the first radiation detector 20A and the second radiographic image captured by the second radiation detector 20B. Hereinafter, the energy subtraction image is referred to as an "ES image" and the image data indicating the energy subtraction image is referred to as "ES image data".

For example, the control unit 80 of the console 18 according to this embodiment subtracts image data obtained by multiplying the first radiographic image data by a predetermined coefficient from image data obtained by multiplying the second radiographic image data by a predetermined coefficient for each corresponding pixel. The control unit 80 generates ES image data indicating an ES image that is a kind of diagnosis image in which soft tissues have been removed and bone tissues have been highlighted, using the subtraction. A method for determining the corresponding pixels of the first radiographic image data and the second radiographic image data is not particularly limited. For example, the amount of positional deviation between the first radiographic image data and the second radiographic image data, which are captured by the radiography apparatus 16 in a state in which a marker is put in advance, is calculated from the difference between the positions of the marker in the first radiographic image data and the second radiographic image data. Then, the corresponding pixels of the first radiographic image data and the second radiographic image data may be determined on the basis of the calculated amount of positional deviation.

In this case, for example, the amount of positional deviation between the first radiographic image data and the second radiographic image data, which are obtained by capturing the image of both the subject W and the marker when the image of the subject W is captured, may be calculated from the difference between the positions of the marker in the first radiographic image data and the second radiographic image data. In addition, for example, the amount of positional deviation between the first radiographic image data and the second radiographic image data may be calculated on the basis of the structure of the subject W in the first radiographic image data and the second radiographic image data obtained by capturing the image of the subject W.

In addition, the control unit 80 of the console 18 according to this embodiment derives bone density as a quantitative value using the first radiographic image captured by the first radiation detector 20A and the second radiographic image captured by the second radiation detector 20B, using a dual-energy X-ray absorptiometry (DXA) method. The invention is not limited to this embodiment and bone mineral content may be derived as the quantitative value.

As an example of a derivation method using the DXA method, the control unit 80 of the console 18 according to this embodiment derives bone density, using the average value of pixel values in a bone tissue region (hereinafter, a "bone region") and the average value of pixel values in a soft tissue region (hereinafter, a "soft region") in a DXA image indicated by DXA image data, which will be described in detail below.

Since the ES image is a radiographic image used for the doctor's diagnosis, it is preferable that the ES image is an image suitable for interpretation. For example, preferably, the ES image is an image in which a tumor mass or calcification as a region of interest (ROI) is easy to see. High-quality images, such as an image which is sharp and whose edge is easy to see, an image with high granularity (the roughness of the image) (fineness), and an image with high contrast, are given as examples of the radiographic image.

Figure 6:
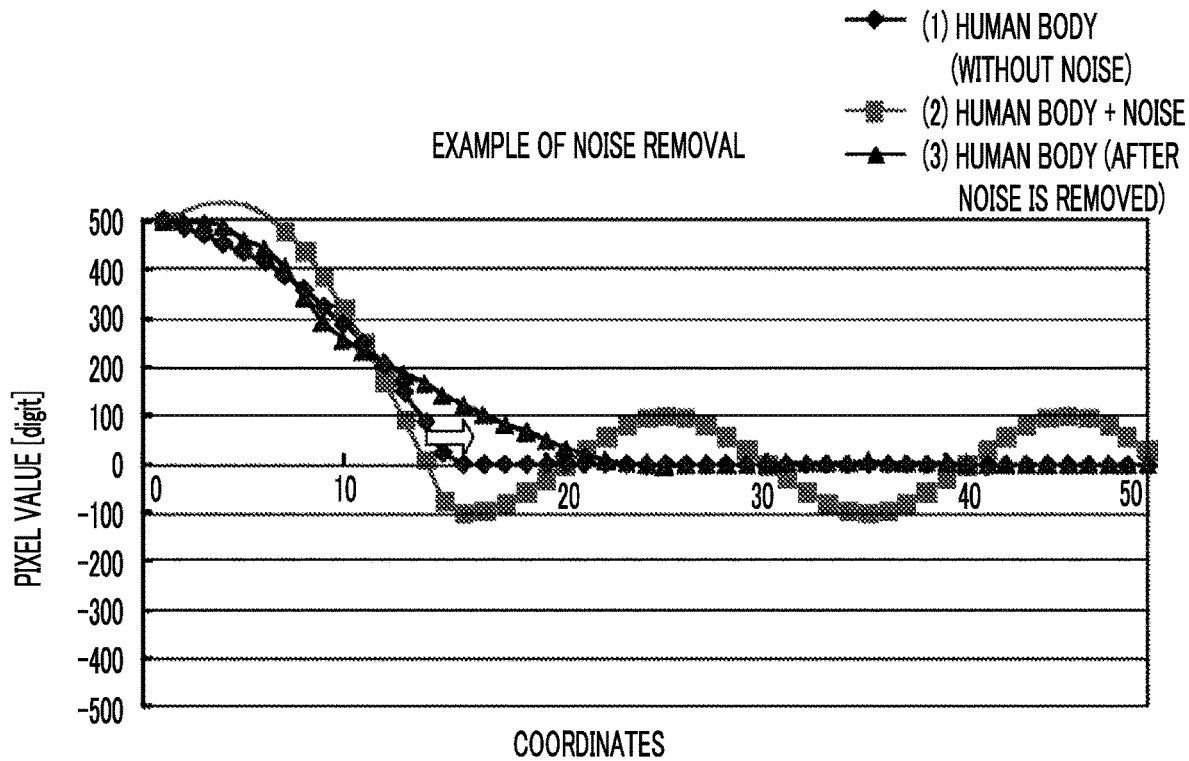
FIG. 6 is a graph illustrating an example of the removal of noise from a radiographic image.

Preferably, in the DXA image used to derive bone density, errors that occur whenever the image of the same subject W is captured in the derived bone density are small (for example, less than 1%), regardless of the visibility of the ROI. An example of the radiographic image is an image which a larger amount of noise than that in the ES image has been removed and an artifact or image blur that is not visible to the doctor has been removed. In a case in which a large amount of noise is removed, the human tissue of a blurred image, such as the skin of the subject W, is likely to be removed. As illustrated in FIG. 6, in the radiographic image of the human tissues, in a case in which noise is removed from a radiographic image (see graph (2) in FIG. 6) including noise by a noise removal process, an edge part of the human body in a radiographic image (see graph (3) in FIG. 6) after noise removal is wider than that in a radiographic image (see graph (1) in FIG. 6) that is not originally affected by noise. Therefore, in a case in which a large amount of noise is removed, an image which has low granularity (is rough) and in which the human tissues of the ROI are blurred is obtained. In addition, in a case in which the DXA image has low granularity (is rough) or a case in which the image of the human tissues of the ROI is blurred, it is possible to ignore influence on the derivation of bone density.

As such, desired image quality (in this embodiment, the amount of noise) is different in the ES image and the DXA image. As described above, the second radiographic image captured by the second radiation detector 20B is more likely to be affected by noise than the first radiographic image captured by the first radiation detector 20A. Therefore, the control unit 80 of the console 18 according to this embodiment performs, as a correction process, a noise removal process suitable for a case in which the ES image is generated and a case in which bone density is derived for the second radiographic image.

Figure 7:
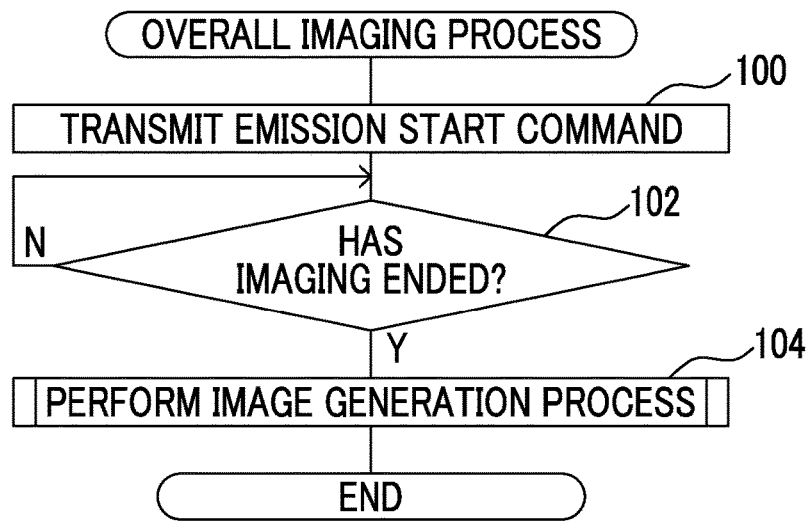
FIG. 7 is a flowchart illustrating an example of the flow of an overall imaging process according to the first embodiment.

Next, the operation of the radiography system 10 according to this embodiment will be described. FIG. 7 is a flowchart illustrating an example of the flow of an overall imaging process performed by the control unit 80 of the console 18. Specifically, the CPU 80A of the control unit 80 executes an overall imaging processing program to perform the overall imaging process illustrated in FIG. 7. The overall imaging processing program is an example of an image processing program according to the present disclosure.

In this embodiment, the overall imaging process illustrated in FIG. 7 is performed in a case in which the control unit 18 of the console 18 acquires an imaging menu including, for example, the name of the subject W, an imaging part, and the emission conditions of the radiation R from the user through the operation unit 90. The control unit 80 may acquire the imaging menu from an external system, such as an RIS, or may acquire the imaging menu input by the user through the operation unit 90.

In Step S100 of FIG. 7, the control unit 80 of the console 18 transmits information included in the imaging menu to the radiography apparatus 16 through the communication unit 92 and transmits the emission conditions of the radiation R to the radiation emitting apparatus 12 through the communication unit 92. Then, the control unit 80 transmits a command to start the emission of the radiation R to the radiography apparatus 16 and the radiation emitting apparatus 12 through the communication unit 92. In a case in which the emission conditions and the emission start command transmitted from the console 18 are received, the radiation emitting apparatus 12 starts the emission of the radiation R according to the received emission conditions. The radiation emitting apparatus 12 may include an irradiation button. In this case, the radiation emitting apparatus 12 receives the emission conditions and the emission start command transmitted from the console 18 and starts the emission of the radiation R according to the received emission conditions in a case in which the irradiation button is pressed.

In the radiography apparatus 16, the first radiation detector 20A captures the first radiographic image and the second radiation detector 20B captures the second radiographic image, on the basis of the information in the imaging menu transmitted from the console 18. In the radiography apparatus 16, the control units 58A and 58B perform various correction processes, such as offset correction and gain correction, for the first radiographic image data indicating the captured first radiographic image and the second radiographic image data indicating the captured second radiographic image, respectively, and store the first radiographic image data and the second radiographic image data subjected to the various correction processes in the storage unit 64.

Then, in Step S102, the control unit 80 determines whether the capture of the radiographic images has ended in the radiography apparatus 16. A method for determining whether the capture of the radiographic images has ended is not particularly limited. For example, each of the control units 58A and 58B of the radiography apparatus 16 transmits end information indicating that imaging has ended to the console 18 through the communication unit 66. In a case in which the end information is received, the control unit 80 of the console 18 determines that the capture of the radiographic images has ended in the radiography apparatus 16. For example, in a case in which each of the control units 58A and 58B transmits the first radiographic image data and the second radiographic image data to the console 18 through the communication unit 66 after imaging ends and the control unit 80 receives the first radiographic image data and the second radiographic image data, the control unit 80 determines that the capture of the radiographic images in the radiography apparatus 16 has ended. In addition, in a case in which the first radiographic image data and the second radiographic image data are received, the console 18 stores the received first radiographic image data and the received second radiographic image data in the storage unit 86.

Then, in a case in which the capture of the radiographic images in the radiography apparatus 16 has not ended, the determination result is "No" and the control unit 80 waits until the capture of the radiographic images in the radiography apparatus 16 ends. On the other hand, in a case in which the capture of the radiographic images in the radiography apparatus 16 has ended, the determination result is "Yes" and the control unit 80 proceeds to Step S104.

Figure 8:
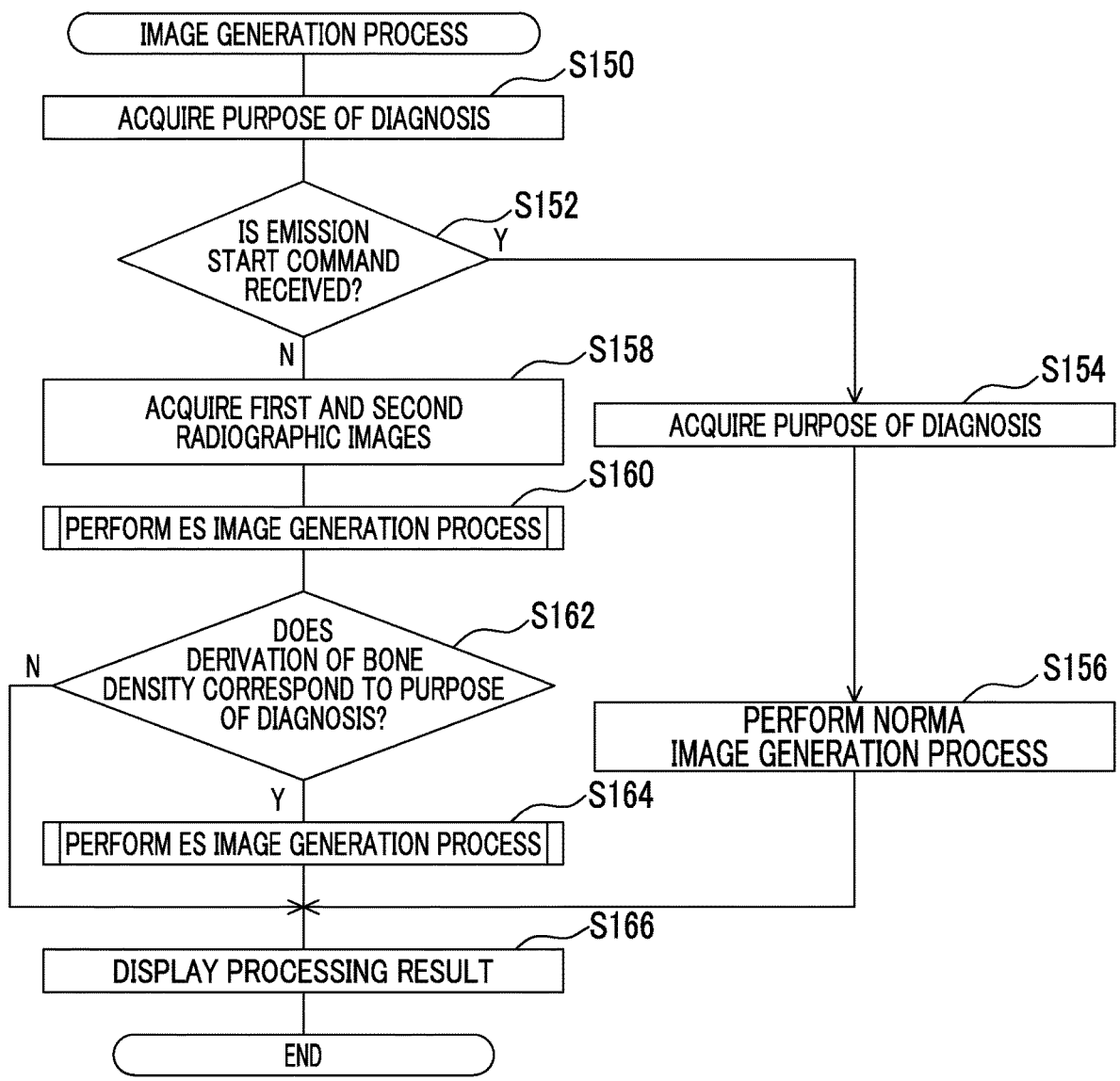
FIG. 8 is a flowchart illustrating an example of the flow of an image generation process in the overall imaging process according to the first embodiment.

In Step S104, the control unit 80 performs an image generation process illustrated in FIG. 8 and ends the overall imaging process.

Next, the image generation process performed in Step S104 of the overall imaging process (see FIG. 7) will be described with reference to FIG. 8.

In Step S150 of FIG. 8, the control unit 80 of the console 18 acquires the user's purpose of diagnosis. A method for acquiring the purpose of diagnosis in the control unit 80 is not particularly limited. In a case in which the purpose of diagnosis is included in the imaging menu, the purpose of diagnosis may be acquired from the imaging menu or the purpose of diagnosis input by the user through the operation unit 90 may be acquired. In the console 18 according to this embodiment, information indicating the correspondence relationship between the purpose of diagnosis and the type of necessary radiographic image or the derivation of bone density is stored in the storage unit 86 in advance. For example, in a case in which the purpose of diagnosis is a "bone fracture", the derivation of bone density is associated with the purpose of diagnosis. In addition, the radiography system 10 according to this embodiment generates the ES image in association with the derivation of bone density. For example, in a case in which the purpose of diagnosis is a "bone tumor", the ES image is associated as the type of radiographic image with the purpose of diagnosis. For example, in a case in which the purpose of diagnosis is an "abdominal tumor", a normal image is associated as the type of radiographic image with the purpose of diagnosis. In this embodiment, the "normal image" is a diagnosis image which is an image other than the ES image and is used for interpretation by the doctor and is a radiographic image captured by so-called normal imaging.

Then, in Step S152, the control unit 80 determines whether to generate the normal image. In a case in which the generation of the normal image is associated with the purpose of diagnosis acquired in Step S150, the control unit 80 determines to generate the normal image and proceeds to Step S154. In Step S154, the control unit 80 acquires the first radiographic image data from the storage unit 86.

Then, in Step S156, the control unit 80 generates a correction process for the acquired first radiographic image data to generate the normal image, stores the normal image in the storage unit 86, and proceeds to Step S166. The correction process performed in this step is the same as a first correction process (which will be described in detail below) that is performed in a case in which the ES image is generated. In addition to the correction process (first correction process), for example, other types of image processing and a noise correction process may be performed. For example, image processing for adjusting the density and brightness of the image in response to a command from the user may be performed as the above-mentioned image processing.

In contrast, in a case in which the derivation of bone density or the generation of the ES image is associated with the purpose of diagnosis, the determination result in Step S152 is "No" and the process proceeds to Step S158. In Step S158, the control unit 80 acquires the first radiographic image data and the second radiographic image data from the storage unit 86.

Figure 9:
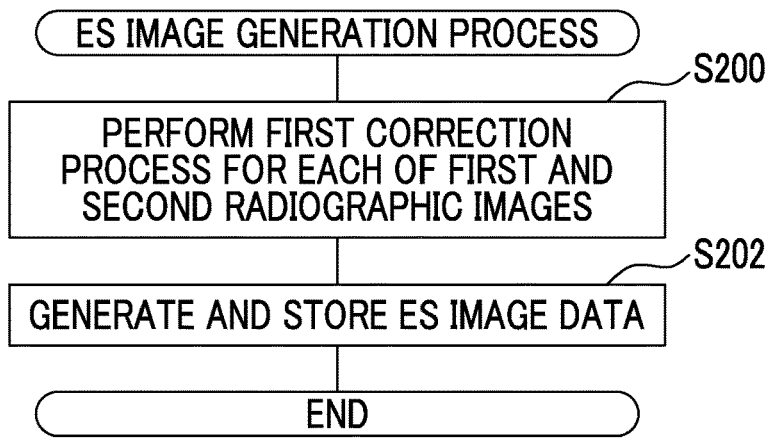
FIG. 9 is a flowchart illustrating an example of the flow of an ES image generation process in the image generation process according to the first embodiment.

In Step S160, the control unit 80 performs an ES image generation process illustrated in FIG. 9. In Step S200 of FIG. 9, the control unit 80 performs the first correction process for each of the first radiographic image data and the second radiographic image data.

In this embodiment, the "first correction process" is a correction process that highlights the edge of human tissues in a state in which the granularity of the corrected radiographic image is high (fine) and removes blur. That is, the first correction process is a correction process that facilitates the doctor's diagnosis (makes it easy for the doctor to see, for example, the ROI). In a case in which the amount of blur to be removed increases, (the amount of noise to be removed increases), the human tissue of a blurred image, such as the skin of the subject W, is likely to be removed. Therefore, in this embodiment, the amount of noise removed by the first correction process is at least smaller than the amount of noise removed by a second correction process which will be described in detail below. For example, specific parameters required to perform the first correction process may be predetermined by experiments using the actual radiography apparatus 16 according to the imaging part.

Then, in Step S202, the control unit 80 generates ES image data using the first radiographic image data and the second radiographic image data subjected to the first correction process in Step S200, using the above-mentioned method, stores the ES image data in the storage unit 86, ends the ES image generation process, and proceeds to Step S162 in the image generation process.

In Step S162, the control unit 80 determines whether the derivation of bone density is associated with the purpose of diagnosis. In a case in which the derivation of bone density is not associated with the purpose of diagnosis, the determination result is "No" and the process proceeds to Step S166. On the other hand, in a case in which the derivation of bone density is associated with the purpose of diagnosis, the determination result in Step S162 is "Yes" and the process proceeds to Step S164.

Figure 10:
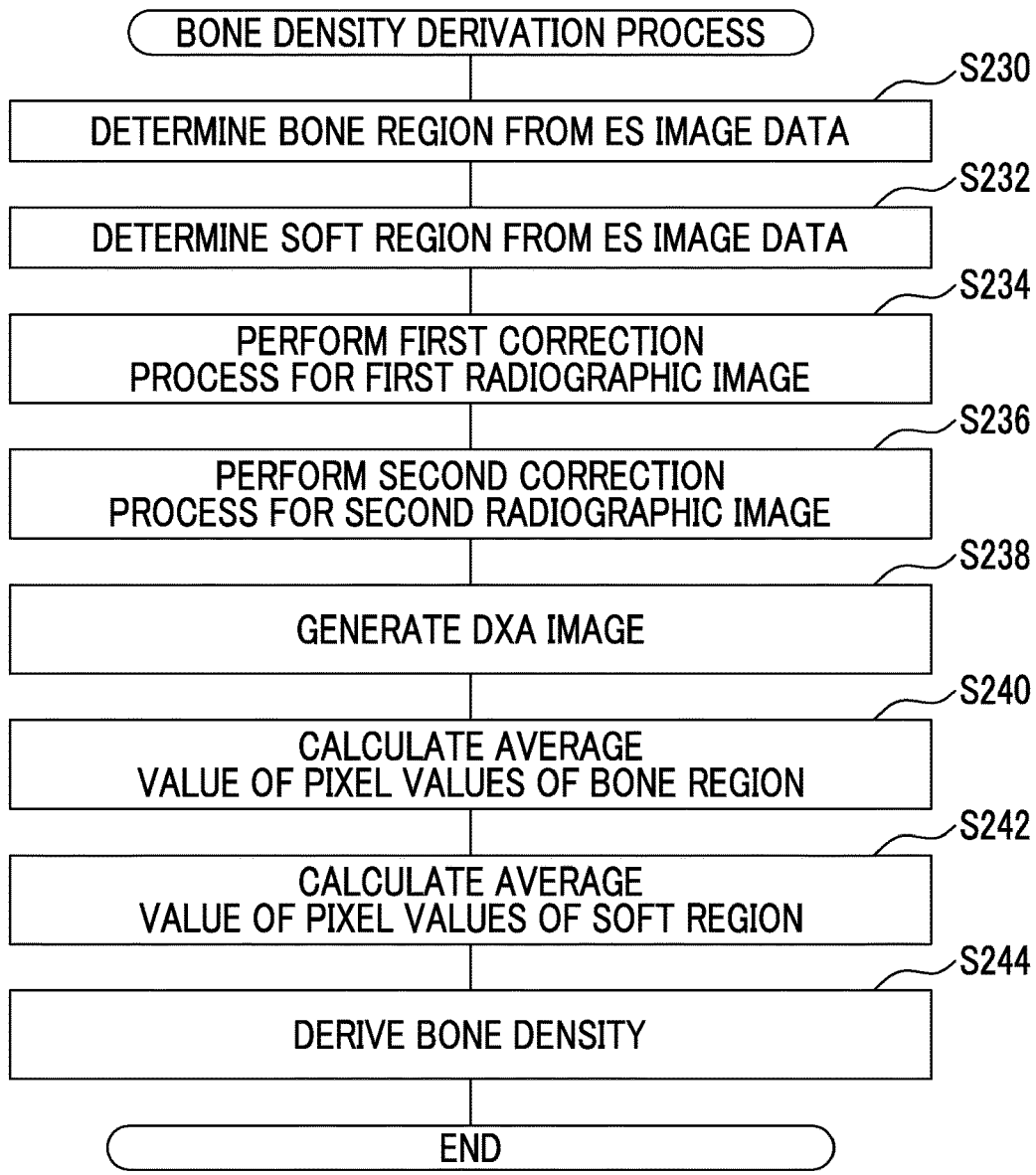
FIG. 10 is a flowchart illustrating an example of the flow of a bone density derivation process in the image generation process according to the first embodiment.

In Step S164, the control unit 80 performs a bone density derivation process illustrated in FIG. 10. In Step S230 of FIG. 10, the control unit 80 determines a bone region in the ES image that is indicated by the ES image data generated by the ES image generation process (see FIG. 9). In this embodiment, for example, the control unit 80 estimates the approximate range of the bone region on the basis of the imaging part included in the imaging menu. Then, the control unit 80 detects pixels that are disposed in the vicinity of the pixels, of which the differential values are equal to or greater than a predetermined value, as the pixels forming the edge (end) of the bone region in the estimated range to determine the bone region.

Figure 11:
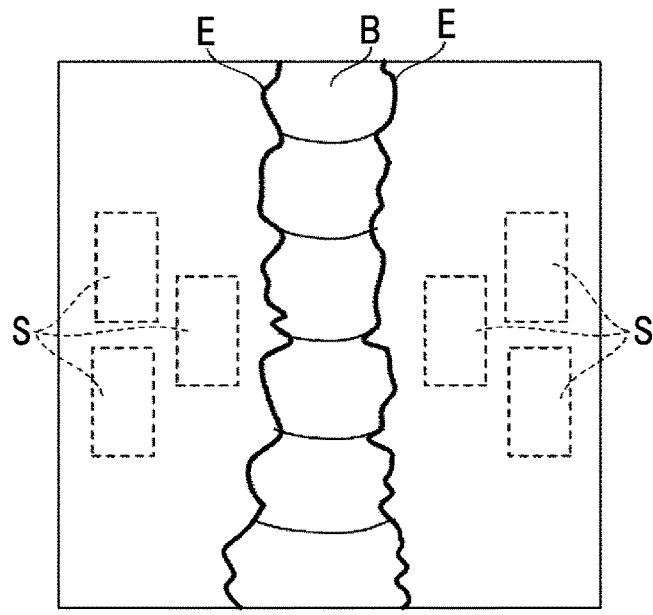
FIG. 11 is a front view schematically illustrating a bone tissue region and a soft tissue region according to the first embodiment.

For example, as illustrated in FIG. 11, in Step S230, the control unit 80 detects the edge E of a bone region B and determines a region in the edge E as the bone region B. For example, FIG. 11 illustrates an ES image in a case in which the image of a backbone part of the upper half of the body of the subject W is captured.

A method for determining the bone region B is not limited to the above-mentioned example. For example, the control unit 80 displays the ES image indicated by the ES image data on the display unit 88. The user designates the edge E of the bone region B in the ES image displayed on the display unit 88 through the operation unit 90. Then, the control unit 80 may determine a region in the edge E designated by the user as the bone region B.

The control unit 80 may display an image in which the ES image and the edge E determined in Step S230 overlap each other on the display unit 88. In a case in which it is necessary to correct the edge E displayed on the display unit 88, the user corrects the position of the edge E through the operation unit 90. Then, the control unit 80 may determine a region in the edge E corrected by the user as the bone region B.

Then, in Step S232, the control unit 80 determines a soft region in the ES image indicated by the ES image data. In this embodiment, for example, the control unit 80 determines, as the soft region, a region which is other than the bone region B and has a predetermined area including pixels at positions that are separated from the edge E by a distance corresponding to a predetermined number of pixels in a predetermined direction. For example, as illustrated in FIG. 11, in Step S232, the control unit 80 determines a plurality of (in the example illustrated in FIG. 11, six) soft regions S.

The predetermined direction and the predetermined number of pixels may be predetermined by, for example, experiments using the actual radiography apparatus 16 according to the imaging part. The predetermined area may be predetermined or may be designated by the user. In addition, for example, the control unit 80 may determine, as a soft region S, the pixels with pixel values in a predetermined range having the minimum pixel value (a pixel value corresponding to a position where the body thickness of the subject W is the maximum except the bone region B) as the lower limit in the ES image data. In addition, it goes without saying that the number of soft regions S determined in Step S232 is not limited to that illustrated in FIG. 11.

Then, in Step S234, the control unit 80 performs the first correction process for the first radiographic image data acquired from the storage unit 86.

Then, in Step S236, the control unit 80 performs the second correction process for the second radiographic image data acquired from the storage unit 86. In this embodiment, the "second correction process" is a correction process that is performed such that a variation in each operation of capturing an image (in this step, the second radiographic image) is within an allowable range. In this embodiment, for example, the control unit 80 performs correction for removing image blur in the entire frequency band of the second radiographic image data. Specifically, the control unit 80 performs, for example, a moving average filtering process, a median filtering process, and a low-pass filtering process to prevent fluctuation in an image average value such that a variation in each imaging operation is within the allowable range. For example, specific parameters required to perform the second correction process may be predetermined by experiments using the actual radiography apparatus 16.

Then, in Step S238, the control unit 80 generates a DXA image using the first radiographic image data subjected to the first correction process in Step S234 and the second radiographic image data subjected to the second correction process in Step S236. In this embodiment, the control unit 80 subtracts image data obtained by multiplying the first radiographic image data subjected to the first correction process in Step S234 by a predetermined coefficient from image data obtained by multiplying the second radiographic image data subjected to the second correction process in Step S236 by a predetermined coefficient for each corresponding pixel, as in the generation of the ES image. The control unit 80 generates DXA image data indicating a DXA image in which soft tissues have been removed and bone tissues have been highlighted, using the subtraction. In some cases, the predetermined coefficient used by the control unit 80 to generate the DXA image and the predetermined coefficient used by the control unit 80 to generate the ES image may be equal to each other or may be different from each other. For example, the predetermined coefficients used to generate each image may be predetermined by experiments using the actual radiography apparatus 16.

Then, in Step S240, the control unit 80 calculates the pixel values of the bone region B in the DXA image data. First, the control unit 80 detects a bone region B corresponding to the bone region B, which has been determined from the ES image data in Step S230, from the DXA image data. Then, the control unit 80 calculates an average value A1 of the pixel values of the detected bone region B as the average value of the pixel values of the bone region B in the DXA image data. Here, a method for determining the bone region B of the DXA image data corresponding to the bone region B of the ES image data is not particularly limited. For example, the determination method may be the same as the method for determining the corresponding pixels of the first radiographic image data and the second radiographic image data in the ES image generation method.

Then, in Step S242, the control unit 80 calculates the pixel values of the entire soft region S in the DXA image data. First, the control unit 80 detects a soft region S corresponding to the entire soft region B, which has been determined from the ES image data in Step S232, from the DXA image data. Then, the control unit 80 calculates an average value A2 of the pixel values of the detected entire soft region S as the average value of the pixel values of the entire soft region S in the DXA image data. Here, in this embodiment, for example, the control unit 80 performs weighting such that the soft region S which is further away from the edge E has a smaller pixel value and calculates the average value A2. A method for determining the soft region S of the DXA image data corresponding to the soft region S of the ES image data is not particularly limited. For example, the determination method may be the same as the method for determining the bone region B of the DXA image data corresponding to the bone region B of the ES image data in Step S240.

Then, in Step S244, the control unit 80 derives the bone density of the imaging part of the subject W and ends the bone density derivation process. In this embodiment, for example, the control unit 80 calculates the difference between the average value A1 calculated in Step S240 and the average value A2 calculated in Step S242. In addition, the control unit 80 multiplies the calculated difference by a conversion coefficient for converting the pixel value into bone mass [g] to calculate the bone mass. Then, the control unit 80 divides the calculated bone mass by the area [cm$^2$] of the bone region B to calculate bone density [g/cm$^2$]. The conversion coefficient may be predetermined by, for example, experiments using the actual radiography apparatus 16 according to the imaging part.

In a case in which the bone density derivation process in Step S164 of the image generation process ends in this way, in Step S166, the control unit 80 displays the processing result on the display unit 88 and ends the image generation process. In the radiography system 10 according to this embodiment, for example, in a case in which the bone density derivation process is performed, the control unit 80 displays, as the processing result, the ES image generated by the ES image generation process in Step S160 and the bone density derived by the bone density generation process in Step S164 on the display unit 88. In addition, in a case in which only the ES image generation process in Step S160 is performed, the control unit 80 displays the generated ES image on the display unit 88. In a case in which the normal image generation process in Step S156 is performed, the control unit 80 displays the generated normal image on the display unit 88. The processing result displayed on the display unit 88 is not limited thereto. For example, in a case in which the bone density derivation process in Step S164 is performed, the control unit 80 may display only the derived bone density on the display unit 88 and may display the DXA image on the display unit 88. The control unit 80 may determine whether to display the ES image or the DXA image depending on the user's selection.

As such, the radiography system 10 according to this embodiment includes the radiography apparatus 16 including the first radiation detector 20A that has a plurality of pixels 32 accumulating charge corresponding to the emitted radiation R and the second radiation detector 20B that is provided so as to be stacked on the side of the first radiation detector 20A from which the radiation R is transmitted and emitted and has a plurality of pixels 32 accumulating charge corresponding to the emitted radiation R. The control unit 80 of the console 18 in the radiography system 10 performs the first correction process for generating a diagnosis image for the second radiographic image captured by the second radiation detector 20B and generates a diagnosis image using the second radiographic image subjected to the first correction process and the first radiographic image captured by the first radiation detector 20A. In addition, the control unit 80 performs the second correction process for deriving a quantitative value for the second radiographic image captured by the second radiation detector 20B and derives bone density using the second radiographic image subjected to the second correction process and the first radiographic image captured by the first radiation detector 20A.

The first correction process and the second correction process performed by the control unit 80 are not limited to this embodiment. For example, so-called optical black correction may be performed as the second correction process. In a case in which the optical black correction is performed, an optical black region used for the optical black correction is provided in the second radiation detector 20B. In an example illustrated in FIG. 12, as illustrated in a plan view, an optical black region 40 may be provided in a region along one side of the second radiation detector 20B on the surface of the second radiation detector 20B, on which the radiation R is incident, and a radiation shield 41 may be provided in the optical black region 40. In the example illustrated in FIG. 12, as illustrated in a side view, the first radiation detector 20A and the second radiation detector 20B are stacked in a state in which the region in which the radiation shield 41 is provided is shifted. However, the first radiation detector 20A and the second radiation detector 20B may be stacked without shifting the region in which the radiation shield 41 is provided. In the side view illustrated in FIG. 12, the radiation limitation member 24 is not illustrated for simplicity of illustration.

Figure 12:
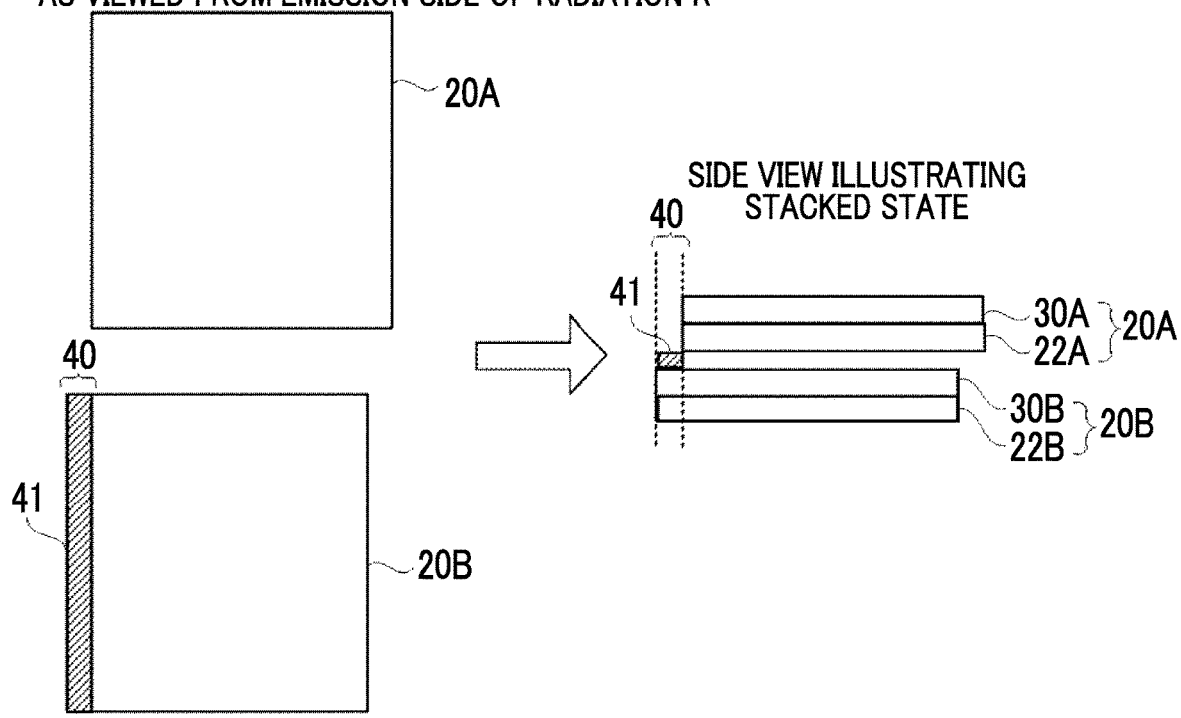
FIG. 12 is an example of a diagram schematically illustrating optical black correction.
Figure 13:
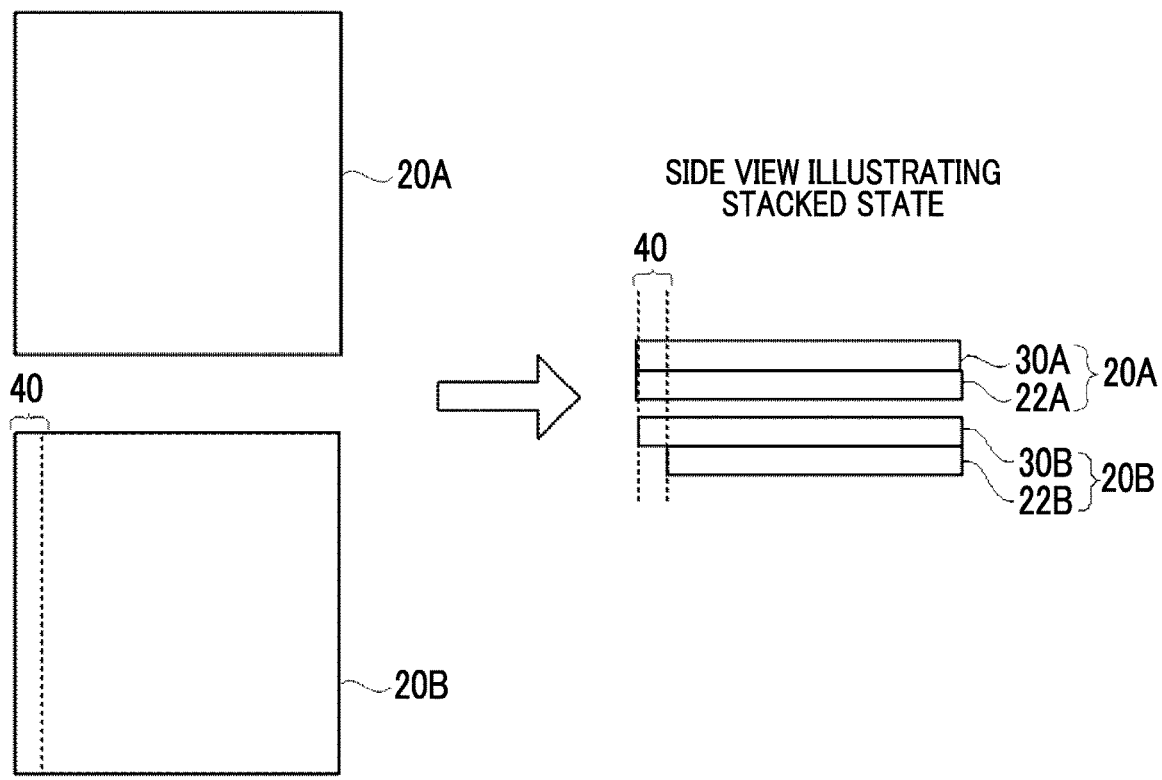
FIG. 13 is another example of the diagram schematically illustrating the optical black correction.

For example, in an example illustrated in FIG. 13, the scintillator 22B is not provided in a region of the second radiation detector 20B which corresponds to the region in which the radiation shield 41 is provided in the example illustrated in FIG. 12. In the example illustrated in FIG. 13, the region in which the scintillator 22B is not provided functions as the optical black region 40. In any of the cases illustrated in FIGS. 12 and 13, the radiation R is not incident on the TFT substrate 30B in the optical black region 40 of the second radiation detector 20B. Therefore, the image of the subject W is not captured in the optical black region 40 of the second radiographic image captured by the second radiation detector 20B.

The control unit 80 of the console 18 stores, for example, the position of the optical black region 40 in the storage unit 86 in advance. In a case in which the second correction process is performed, image data in a region other than the optical black region 40 is corrected using the image data in the optical black region 40 of the second radiographic image to remove so-called streak unevenness from the second radiographic image data. In a case in which the normal image is generated, the control unit 80 generates the normal image from the first radiographic image captured by the first radiation detector 20A as described in this embodiment. In contrast, in a case in which the ES image and the DXA image are generated, the control unit 80 generates the ES image and the DXA image using image data in a region other than the optical black region 40 of the second radiographic image data and image data in a region of the first radiographic image data which corresponds to the region other than the optical black region 40 of the second radiographic image.

An optical black correction method is not limited to the above-mentioned method. In addition, the position and size of the optical black region 40 are not limited to the examples illustrated in FIGS. 12 and 13. For example, instead of the side of the second radiation detector 20B along which the optical black regions 40 illustrated in FIGS. 12 and 13 are provided, the optical black region 40 may be provided along a side adjacent to the side or the optical black region 40 may be provided along a plurality of sides of the second radiation detector 20B. As the optical black region 40 is provided at a larger number of positions and the total size of the optical black region 40 becomes larger, the accuracy of correction by the optical black correction becomes higher. However, the region in which the image of the subject W is captured in the second radiation detector 20B is reduced. Therefore, for example, the position and total size of the optical black region 40 may be predetermined by experiments using the actual radiography apparatus 16 according to the imaging part.

Second Embodiment

In the first embodiment, the case in which the console 18 performs the first correction process and the second correction process has been described. However, in this embodiment, a case in which the radiography apparatus 16 performs the first correction process and the second correction process will be described.

Since the configuration of the radiography system 10, the radiography apparatus 16, and the console 18 is the same as that in the first embodiment (see FIGS. 1 to 4), the description thereof will not be repeated.

Since the flow of the overall imaging process performed by the control unit 80 of the console 18 according to this embodiment is the same as the flow of the overall imaging process (see FIG. 7) in the first embodiment, the description thereof will not be repeated.

In this embodiment, the radiography apparatus 16 is different from the radiography apparatus 16 according to the first embodiment in an operation of acquiring offset data that is used for offset correction in the first radiation detector 20A and the second radiation detector 20B of the radiography apparatus 16.

The operation of acquiring the offset data of the first radiation detector 20A and the second radiation detector 20B of the radiography apparatus 16 according to this embodiment will be described. In general, random noise is likely to overlap the offset data. Therefore, the offset data is acquired a plurality of times. For example, the offset data is continuously acquired. Then, offset correction is performed using the average value of the offset data acquired a plurality of times. Since the offset data is acquired a plurality of times, it takes a lot of time to acquire the offset data. In a general radiography apparatus or the radiography apparatus 16 according to the first embodiment, for example, in a state in which the radiography apparatus, for example, the first radiation detector 20A and the second radiation detector 20B in the first embodiment are turned on and operate stably, the offset data is acquired in advance at a predetermined time before radiographic images are captured. The radiography apparatus 16 according to this embodiment also acquires the offset data of the first radiation detector 20A and the second radiation detector 20B a predetermined number of times (a plurality of times) in advance as described above.

The radiography apparatus 16 according to this embodiment further acquires the offset data of the second radiation detector 20B in a case in which the emission start command transmitted by the console 18 in Step S100 of the overall imaging process (see FIG. 7) is received. That is, the radiography apparatus 16 acquires the offset data of the second radiation detector 20B immediately before the second radiation detector 20B captures a radiographic image. In this case, since the period from the reception of the emission start command by the radiography apparatus 16 to the emission of the radiation R to the second radiation detector 20B is short, the offset data is acquired one time or at least the number of times that is less than that in a case in which the offset data is acquired in advance. In this case, the time when the offset data is acquired is preferably close to the time when the second radiation detector 20B is irradiated with the radiation R.

The radiography apparatus 16 according to this embodiment is different from the radiography apparatus 16 according to the first embodiment in that the control unit 58A performs the first correction process for the image data stored in the image memory 56A and the control unit 58B performs the first correction process and the second correction process for the image data stored in the image memory 56B.

In the radiography system 10 according to this embodiment, as described above, the process of correcting image data using the average value of the offset data acquired in advance is referred to as the first correction process. In addition, in the radiography system 10 according to this embodiment, as described above, the process of correcting image data using the offset data acquired immediately before a radiographic image is captured is referred to as the second correction process.

Since the first correction process is performed using the average value of a plurality of offset data items acquired in advance, the image data is corrected using the offset data (average value) that is less affected by random noise. As a result, the first radiographic image and a second radiographic image A obtained by the first correction process are high-granularity (fine) images.

However, in a case in which the offset data is acquired in advance, with the lapse of time until a radiographic image is actually captured, the temperature of the radiography apparatus 16 is likely to vary according to, for example, a change in environment and a change in the usage of the radiography apparatus 16. In this case, a signal is likely to be changed by the influence of the temperature change and the offset data is likely to be inappropriate. In contrast, in the second correction process, the image data is corrected using the offset data acquired immediately before imaging. Since the temperature in a case in which a radiographic image is actually captured is close to the temperature in a case in which the offset data is acquired, the amount of noise removed from a second radiographic image B obtained by the second correction process is more than the amount of noise removed from the second radiographic image A (first radiographic image) obtained by the first correction process. In addition, since the number of offset data items acquired by the second correction process is less than the number of offset data items acquired by the first correction process as described above, the second radiographic image B obtained by the second correction process has a lower granularity (is coarser) than the second radiographic image A (first radiographic image) obtained by the first correction process. However, as described in the first embodiment, influence on the derivation of bone density is negligible.

Figure 14:
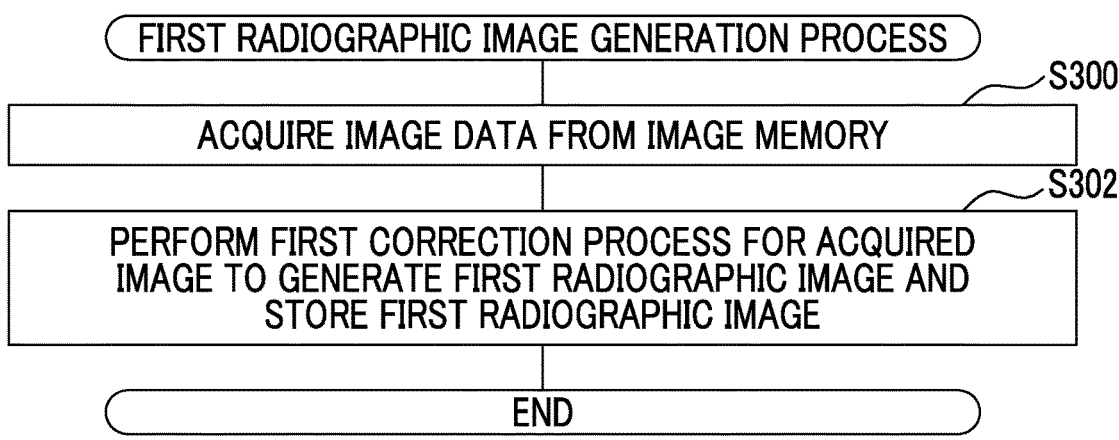
FIG. 14 is a flowchart illustrating an example of the flow of a first radiographic image generation process according to a second embodiment.

After the image data read from the first radiation detector 20A is stored in the image memory 56A, the control unit 58A performs a first radiographic image generation process illustrated in FIG. 14. A first radiographic image generation processing program illustrated in FIG. 14 is stored in the memory 62 in advance and the CPU 60 executes the first radiographic image generation processing program to perform the first radiographic image generation process illustrated in FIG. 14.

As illustrated in FIG. 14, in Step S300, the control unit 58A acquires image data from the image memory 56A.

Then, in Step S302, the control unit 58A performs the first correction process for the acquired image data to generate image data of the first radiographic image, stores the image data in the image memory 56A, and ends the first radiographic image generation process.

Figure 15:
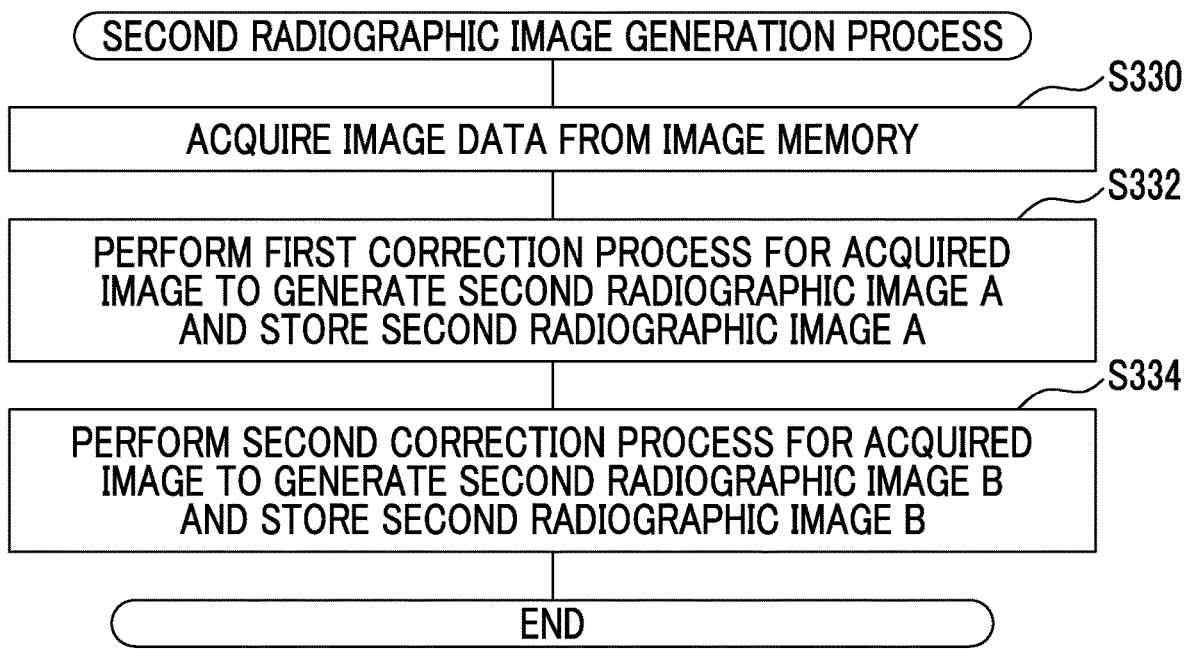
FIG. 15 is a flowchart illustrating an example of the flow of a second radiographic image generation process according to the second embodiment.

In contrast, the control unit 58B stores the image data read from second radiation detector 20B in the image memory 56B and performs a second radiographic image generation process illustrated in FIG. 15. A second radiographic image generation processing program illustrated in FIG. 15 is stored in the memory 62 in advance and the CPU 60 executes the second radiographic image generation processing program to perform the second radiographic image generation process illustrated in FIG. 15.

As illustrated in FIG. 15, in Step S330, the control unit 58B acquires image data from the image memory 56B.

In Step S332, the control unit 58B performs the first correction process for the acquired image data to generate image data of the second radiographic image A and stores the image data in the image memory 56B.

Then, in Step S234, the control unit 58B performs the second correction process for the acquired image data to generate image data of the second radiographic image B, stores the image data in the image memory 56B, and ends the second radiographic image generation process. As such, in this embodiment, image data items (hereinafter, referred to as "second radiographic image data A" and "second radiographic image data B") of two types of second radiographic images (second radiographic images A and B) are generated. The second radiographic images A and B are transmitted from the radiography apparatus 16 to the console 18 through the communication unit 66.

The flow of the image generation process in the control unit 80 of the console 18 is the same as the flow of the image generation process (see FIG. 8) according to the first embodiment except that the second radiographic image data items A and B are acquired as the image data of the second radiographic image in Step S158.

The second radiographic image data A of the second radiographic image A is used to generate a normal image and the ES image. The second radiographic image data B of the second radiographic image B is used to derive bone density (to generate the DXA image).

Figure 16:
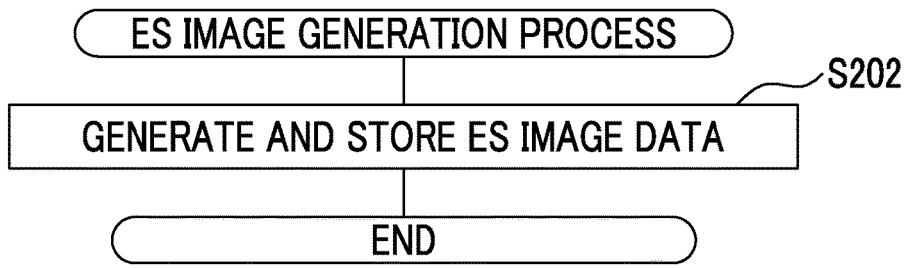
FIG. 16 is a flowchart illustrating an example of the flow of an ES image generation process in the image generation process according to the second embodiment.

An ES image generation process performed by the control unit 80 of the console 18 according to this embodiment differs from the ES image generation process (see FIG. 9) according to the first embodiment in that the process in Step S200 is not performed as illustrated in FIG. 16.

In Step S202 of the ES image generation process according to this embodiment, the control unit 80 generates ES image data using the first radiographic image data acquired from the storage unit 86 and the second radiographic image data A acquired from the storage unit 86, using the above-mentioned method.

Figure 17:
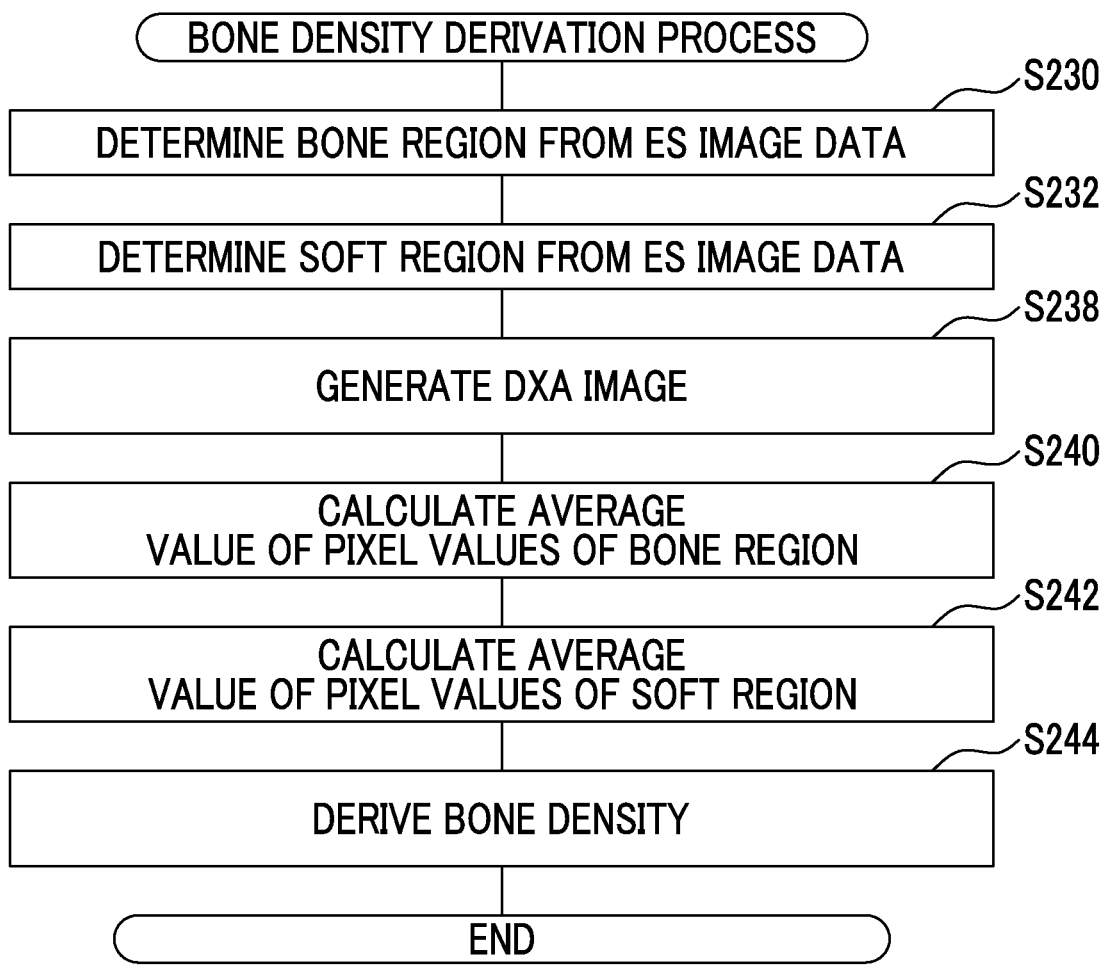
FIG. 17 is a flowchart illustrating an example of the flow of a bone density derivation process in the image generation process according to the second embodiment.

In contrast, a bone density derivation process performed by the control unit 80 of the console 18 according to this embodiment differs from the bone density derivation process (see FIG. 10) according to the first embodiment in that Steps S234 and S236 are not performed as illustrated in FIG. 17.

In Step S238 of the bone density derivation process according to this embodiment, the control unit 80 generates a DXA image using the first radiographic image data acquired from the storage unit 86 and the second radiographic image data B acquired from the storage unit 86.

As such, the radiography system 10 according to this embodiment includes the radiography apparatus 16 including the first radiation detector 20A that has a plurality of pixels 32 accumulating charge corresponding to the emitted radiation R and the second radiation detector 20B that is provided so as to be stacked on the side of the first radiation detector 20A from which the radiation R is transmitted and emitted and has a plurality of pixels 32 accumulating charge corresponding to the emitted radiation R. The control unit 58A of the radiography apparatus 16 performs first control including control for reading the charge from the plurality of pixels 32 of the first radiation detector 20A and control for reading the charge from the plurality of pixels 32 of the second radiation detector 20B and performing the first correction process for generating a diagnosis image for the image data obtained by the read charge in a case in which the diagnosis image is generated. In addition, the control unit 58A of the radiography apparatus 16 performs second control including control for reading charge from the plurality of pixels 32 of the first radiation detector 20A and control for reading the charge from the plurality of pixels 32 of the second radiation detector 20B and performing the second correction process for deriving a quantitative value for the image data obtained by the read charge in a case in which bone density is derived. Then, the control unit 80 of the console 18 generates a diagnosis image using the first radiographic image and the second radiographic image obtained by the first control. In addition, the control unit 80 derives bone density using the first radiographic image and the second radiographic image obtained by the second control.

In this embodiment, the case in which the control units 58A and 58B perform at least one of the first correction process or the second correction process has been described. However, the control units 58A and 58B may further perform, for example, other correction processes and other types of image processing.

In the radiography system 10 according to this embodiment, the radiography apparatus 16 performs the first correction process and the second correction process which are the offset process. However, the control unit 80 of the console 18 may perform the first correction process and the second correction process. In this case, the radiography apparatus 16 transmits, to the console 18, the image data for generating the first radiographic image data and the image data for generating the second radiographic image data items A and B which have not been subjected to the offset process and two types of offset data (the average value of the offset data acquired in advance and the offset data acquired immediately before imaging). The control unit 80 that has received the image data and two types of offset data may perform the same processes as the first radiographic image generation process (see FIG. 14) and the second radiographic image generation process (see FIG. 15) to generate the first radiographic image and the second radiographic images A and B.

In addition, this embodiment and the first embodiment may be combined with each other. That is, after the radiography apparatus 16 performs the first correction process and the second correction process which are the offset process, the console 18 may perform the first correction process and the second correction process for removing blur or artifacts.

The first correction process and the second correction process performed by the radiography apparatus 16 are not limited to this embodiment. For example, processes in which the amplification factors of an amplification circuit of the signal processing unit 54B of the radiography apparatus 16 (for example, in a case in which the amplification circuit includes an amplifier, the gain of the amplifier) are different from each other may be performed as the first correction process and the second correction process. As the gain of the amplifier increases, a dynamic range is reduced and the influence of noise generated in the process after conversion by the A/D converter of the signal processing unit 54B is reduced. Therefore, in a case in which a diagnosis image (a normal image and an ES image) is generated, the control unit 58B of the radiography apparatus 16 may perform the first correction process that sets the gain of the amplifier to a first gain and amplifies an electric signal indicating image data. In a case in which bone density is derived, the control unit 58B may perform the second correction process that sets the gain of the amplifier to a second gain higher than the first gain and amplifies the electric signal indicating image data. The control unit 58A may perform the first correction process both in the case in which the diagnosis image is generated and in the case in which bone density is derived. In this case, the control unit 80 of the console 18 detects the bone region B and the soft region S from the DXA image in the derivation of bone density.

For example, in the process of reading charge from the pixels 32 of the second radiation detector 20B, a process of reading charge from each pixel 32 may be the first correction process and a process of collectively reading charge from a plurality of pixels 32 may be the second correction process. In a case in which charge is collectively read from a plurality of pixels 32, the resolution of the image is reduced, but the amount of electrical noise that overlaps image data is reduced. Therefore, the control unit 58B of the radiography apparatus 16 may perform the first correction process of reading charge from each pixel 32 of the second radiation detector 20B in a case in which a diagnosis image (a normal image and an ES image) is generated and may perform the second correction process of collectively reading charge from a plurality of pixels 32 of the second radiation detector 20B in a case in which bone density is derived. In addition, if a case in which charge is collectively read from four (=2×2) pixels 32 is given as an example of a method for collectively reading charge from a plurality of pixels 32, the control unit 58B may direct the gate line driver 52B to output a control signal for turning on the thin film transistors 32C to two adjacent gate lines 34 at the same time and may add electric signals that flow through two adjacent data lines 36.

In addition, the control unit 80 of the console 18 may generate the ES image using the image data of the first radiographic image generated by reading charge from each pixel 32 and the image data of the second radiographic image generated by collectively reading charge from a plurality of pixels 32. However, in a case in which charge is collectively read from the plurality of pixels 32, resolution is reduced. Therefore, in a case in which the user wants a high-resolution ES image, it is preferable not to collectively read charge from the plurality of pixels 32.

As described above, the radiography apparatus 16 of the radiography system 10 according to each of the above-described embodiments includes the first radiation detector 20A that has a plurality of pixels 32 accumulating charge corresponding to the emitted radiation R and the second radiation detector 20B that is provided so as to be stacked on the side of the first radiation detector 20A from which the radiation R is transmitted and emitted and has a plurality of pixels 32 accumulating charge corresponding to the emitted radiation R.

The radiography system 10 performs the first correction process for generating a diagnosis image for the second radiographic image captured by the second radiation detector 20B and performs the second correction process for deriving bone density for the second radiographic image. The control unit 80 of the console 18 generates a diagnosis image using the first radiographic image and the second radiographic image subjected to the first correction process and derives bone density using the first radiographic image and the second radiographic image subjected to the second correction process.

Therefore, according to the radiography system 10 of each of the above-described embodiments, it is possible to obtain a high-quality diagnosis image and at least one of a high-accuracy bone mineral content value or bone density.

In each of the above-described embodiments, the case in which the amount of noise removed by the first correction process is different from the amount of noise removed by the second correction process, specifically, the amount of noise removed by the second correction process is more than the amount of noise removed by the first correction process has been described. However, the invention is not limited thereto. For example, the type of noise removed by the first correction process may be different from the type of noise removed by the second correction process. The second correction process may not remove noise which does not have an effect on the derivation of bone density, for example, noise which does not change whenever imaging is performed and uniformly overlaps the image.

In each of the above-described embodiments, the case in which an indirect-conversion-type radiation detector that converts radiation into light and converts the converted light into charge is applied to both the first radiation detector 20A and the second radiation detector 20B has been described. However, the invention is not limited thereto. For example, a direct-conversion-type radiation detector that directly converts radiation into charge may be applied to at least one of the first radiation detector 20A or the second radiation detector 20B.

In each of the above-described embodiments, the case in which the irradiation side sampling radiation detectors in which the radiation R is incident from the TFT substrates 30A and 30B are applied to the first radiation detector 20A and the second radiation detector 20B, respectively, has been described. However, the invention is not limited thereto. For example, a so-called penetration side sampling (PSS) radiation detector in which the radiation R is incident from the scintillator 22A or 22B may be applied to at least one of the first radiation detector 20A or the second radiation detector 20B.

In the above-described embodiments, the case in which the radiography apparatus 16 is controlled by two control units (control units 58A and 58B) has been described. However, the invention is not limited thereto. For example, the radiography apparatus 16 may be controlled by one control unit.

In each of the above-described embodiments, the aspect in which the overall imaging processing program is stored (installed) in the ROM 80B in advance has been described. However, the invention is not limited thereto. The overall imaging processing program may be recorded on a recording medium, such as a compact disk read only memory (CD-ROM), a digital versatile disk read only memory (DVD-ROM), or a universal serial bus (USB) memory, and then provided. In addition, the overall imaging processing program may be downloaded from an external apparatus through the network.

The disclosure of Japanese Patent Application No. 2016-063952, filed on Mar. 28, 2016, is incorporated herein by reference in its entirety.

All publications, patent applications, and technical standards mentioned in this specification are herein incorporated by reference to the same extent as if each individual publication, patent application, or technical standard is specifically and individually indicated to be incorporated by reference.

EXPLANATION OF REFERENCES

10: radiography system
12: radiation emitting apparatus
14: radiation source
16: radiography apparatus
18: console
20A: first radiation detector
20B: second radiation detector
21: housing
22A, 22B: scintillator
24: radiation limitation member
26A, 26B: control substrate
28: case
30A, 30B: TFT substrate
32: pixel
32A: sensor unit
32B: capacitor
32C: thin film transistor
34: gate line
36: data line
40: optical black region
41: radiation shield
52A, 52B: gate line driver
54A, 54B: signal processing unit
56A, 56B: image memory
58A, 58B, 80: control unit
60, 80A: CPU
62: memory
64, 86: storage unit
66, 92: communication unit
70: power supply unit
80B: ROM
80C: RAM
88: display unit
90: operation unit
94: bus
B: bone region
E: edge
L1: solid line
L2: solid line
R: radiation
S: soft region
W: subject

What is claimed is:

1. A radiography system comprising:
a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation;
a generation unit that performs a first correction process for generating a diagnosis image for a second radiographic image captured by the second radiation detector and generates the diagnosis image, using the second radiographic image subjected to the first correction process and a first radiographic image captured by the first radiation detector; and
a derivation unit that performs a second correction process for deriving a quantitative value for the second radiographic image captured by the second radiation detector and derives at least one of bone mineral content or bone density, using the second radiographic image subjected to the second correction process and the first radiographic image captured by the first radiation detector.

2. The radiography system according to claim 1,
wherein the second correction process is at least one of a correction process in which the amount of noise removed is more than the amount of noise removed in the first correction process or a correction process in which the amount of noise allowed in a processing result is less than the amount of noise allowed in a processing result of the first correction process.

3. The radiography system according to claim 1,
wherein the first correction process is a correction process that removes a visible artifact in the diagnosis image.

4. The radiography system according to claim 1,
wherein the second correction process is a correction process that prevents a variation in an average value of pixel values in each of a soft tissue region and a bone tissue region of a corrected second radiographic image after the second correction process in each imaging operation.

5. The radiography system according to claim 1, further comprising:
a radiation limitation member that limits the transmission of the radiation between the first radiation detector and the second radiation detector.

6. The radiography system according to claim 1,
wherein each of the first radiation detector and the second radiation detector comprises a light emitting layer that is irradiated with the radiation and emits light,
the plurality of pixels of each of the first radiation detector and the second radiation detector receive the light, generate the charge, and accumulate the charge, and
the light emitting layer of the first radiation detector and the light emitting layer of the second radiation detector have different compositions.

7. The radiography system according to claim 6,
wherein the light emitting layer of the first radiation detector includes CsI, and
the light emitting layer of the second radiation detector includes GOS.

8. The radiography system according to claim 1,
wherein each of the first radiation detector and the second radiation detector comprises a light emitting layer that is irradiated with the radiation and emits light and a substrate provided with the plurality of pixels which receive the light, generate the charge, and accumulate the charge, and
the substrate is stacked on a side of the light emitting layer on which the radiation is incident.

9. A radiography system comprising:
a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation;

a control unit that performs first control including control for reading charge from a plurality of pixels of the first radiation detector and control for reading charge from a plurality of pixels of the second radiation detector and performing a first correction process for generating a diagnosis image for image data obtained by the read charge that is read from the second radiation detector in a case in which the diagnosis image is generated and performs second control including control for reading charge from the plurality of pixels of the first radiation detector and control for reading charge from the plurality of pixels of the second radiation detector and performing a second correction process for deriving a quantitative value for image data obtained by the read charge that is read from the second radiation detector in a case in which the quantitative value is derived;

a generation unit that generates the diagnosis image, using a first radiographic image and a second radiographic image obtained by the first control; and a derivation unit that derives at least one of bone mineral content or bone density, using a first radiographic image and a second radiographic image obtained by the second control.

10. An image processing method comprising:

allowing an acquisition unit to acquire a first radiographic image and a second radiographic image from a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation;

allowing a generation unit to perform a first correction process for generating a diagnosis image for the second radiographic image captured by the second radiation detector and to generate the diagnosis image, using the second radiographic image subjected to the first correction process and the first radiographic image captured by the first radiation detector; and allowing a derivation unit to perform a second correction process for deriving a quantitative value for the second radiographic image captured by the second radiation detector and to derive at least one of bone mineral content or bone density, using the second radiographic image subjected to the second correction process and the first radiographic image captured by the first radiation detector.

11. A non-transitory computer readable medium storing a program that causes a computer to execute a process, the process comprising:

acquiring a first radiographic image and a second radiographic image from a radiography apparatus comprising a first radiation detector that includes a plurality of pixels accumulating charge corresponding to emitted radiation and a second radiation detector that is provided so as to be stacked on a side of the first radiation detector from which the radiation is transmitted and emitted and includes a plurality of pixels accumulating charge corresponding to the emitted radiation;

performing a first correction process for generating a diagnosis image for the second radiographic image captured by the second radiation detector and generating the diagnosis image, using the second radiographic image subjected to the first correction process and the first radiographic image captured by the first radiation detector; and performing a second correction process for deriving a quantitative value for the second radiographic image captured by the second radiation detector and deriving at least one of bone mineral content or bone density, using the second radiographic image subjected to the second correction process and the first radiographic image captured by the first radiation detector.

* * * * *